US011712176B2

(12) United States Patent
Addison et al.

(10) Patent No.: US 11,712,176 B2
(45) Date of Patent: Aug. 1, 2023

(54) SYSTEMS AND METHODS FOR VIDEO-BASED NON-CONTACT TIDAL VOLUME MONITORING

(71) Applicant: Covidien LP, Mansfield, MA (US)

(72) Inventors: Paul S. Addison, Midlothian (GB); Dominique Jacquel, Edinburgh (GB); David Ming Hui Foo, Glasgow (GB)

(73) Assignee: Covidien, LP, Mansfield, MA (US)

( * ) Notice: Subject to any disclaimer, the term of this patent is extended or adjusted under 35 U.S.C. 154(b) by 1150 days.

(21) Appl. No.: 16/219,360

(22) Filed: Dec. 13, 2018

(65) Prior Publication Data
US 2019/0209046 A1    Jul. 11, 2019

Related U.S. Application Data

(60) Provisional application No. 62/614,763, filed on Jan. 8, 2018.

(51) Int. Cl.
*G06T 15/00*     (2011.01)
*A61B 5/091*     (2006.01)
(Continued)

(52) U.S. Cl.
CPC ............ *A61B 5/091* (2013.01); *A61B 5/0077* (2013.01); *A61B 5/1135* (2013.01);
(Continued)

(58) Field of Classification Search
CPC ... A61B 5/7485; A61B 5/1135; A61B 5/0077; A61B 5/091; G06T 7/0014;
(Continued)

(56) References Cited

U.S. PATENT DOCUMENTS

| 5,107,845 A | 4/1992 | Guern et al. |
| 5,408,998 A | 4/1995 | Mersch |

(Continued)

FOREIGN PATENT DOCUMENTS

| CN | 106725410 A | 5/2017 |
| CN | 111728602 A | 10/2020 |

(Continued)

OTHER PUBLICATIONS

Yu MC, Liou JL, Kuo SW, Lee MS, Hung YP. Noncontact respiratory measurement of volume change using depth camera. In2012 Annual International Conference of the IEEE Engineering in Medicine and Biology Society Aug. 28, 2012 (pp. 2371-2374). IEEE.*

(Continued)

*Primary Examiner* — Phu K Nguyen
(74) *Attorney, Agent, or Firm* — Holzer Patel Drennan

(57) ABSTRACT

The present invention relates to the field of medical monitoring, and in particular non-contact video monitoring to measure tidal volume of a patient. Systems, methods, and computer readable media are described for determining a region of interest of a patient and monitoring that region of interest to determine tidal volume of the patient. This may be accomplished using a depth sensing camera to monitor a patient and determine how their chest and/or other body parts are moving as the patient breathes. This sensing of movement can be used to determine the tidal volume measurement.

19 Claims, 26 Drawing Sheets

(51) Int. Cl.
*A61B 5/113* (2006.01)
*A61B 5/00* (2006.01)
*G06T 7/70* (2017.01)
*G06T 7/00* (2017.01)

(52) U.S. Cl.
CPC .......... *A61B 5/7485* (2013.01); *G06T 7/0014* (2013.01); *G06T 7/70* (2017.01); *G06T 2207/10016* (2013.01); *G06T 2207/10028* (2013.01); *G06T 2207/30196* (2013.01)

(58) Field of Classification Search
CPC . G06T 2207/10028; G06T 2207/10016; G06T 2207/30196; G06T 7/70
USPC ........................................................ 345/418
See application file for complete search history.

(56) References Cited

U.S. PATENT DOCUMENTS

| | | |
|---|---|---|
| 5,704,367 A | 1/1998 | Ishikawa et al. |
| 5,800,360 A | 9/1998 | Kisner et al. |
| 5,995,856 A | 11/1999 | Mannheimer et al. |
| 6,668,071 B1 | 12/2003 | Minkin et al. |
| 6,920,236 B2 | 7/2005 | Prokoski |
| 7,431,700 B2 | 10/2008 | Aoki et al. |
| 7,558,618 B1 | 7/2009 | Williams |
| 8,149,273 B2 | 4/2012 | Liu et al. |
| 8,754,772 B2 | 6/2014 | Horng et al. |
| 8,792,969 B2 | 7/2014 | Bernal et al. |
| 8,971,985 B2 | 3/2015 | Bernal et al. |
| 9,226,691 B2 | 1/2016 | Bernal et al. |
| 9,282,725 B2 | 3/2016 | Jensen-Jarolim et al. |
| 9,301,710 B2 | 4/2016 | Mestha et al. |
| 9,402,601 B1 | 8/2016 | Berger et al. |
| 9,436,984 B2 | 9/2016 | Xu et al. |
| 9,443,289 B2 | 9/2016 | Xu et al. |
| 9,504,426 B2 | 11/2016 | Kyal et al. |
| 9,662,022 B2 | 5/2017 | Kyal et al. |
| 9,693,693 B2 | 7/2017 | Farag et al. |
| 9,693,710 B2 | 7/2017 | Mestha et al. |
| 9,697,599 B2 | 7/2017 | Prasad et al. |
| 9,750,461 B1 | 9/2017 | Telfort |
| 9,839,756 B2 | 12/2017 | Klasek |
| 9,943,371 B2 | 4/2018 | Bresch et al. |
| 10,278,585 B2 | 5/2019 | Ferguson et al. |
| 10,376,147 B2 | 8/2019 | Wood et al. |
| 10,398,353 B2 | 9/2019 | Addison et al. |
| 10,523,852 B2 | 12/2019 | Tzvieli et al. |
| 10,588,779 B2 | 3/2020 | Vorhees et al. |
| 10,650,585 B2 * | 5/2020 | Kiely ...................... A61B 6/50 |
| 10,667,723 B2 | 6/2020 | Jacquel et al. |
| 10,702,188 B2 | 7/2020 | Addison et al. |
| 10,874,331 B2 | 12/2020 | Kaiser et al. |
| 10,939,824 B2 | 3/2021 | Addison et al. |
| 10,939,834 B2 | 3/2021 | Khwaja et al. |
| 2002/0137464 A1 | 9/2002 | Dolgonos et al. |
| 2004/0001633 A1 | 1/2004 | Caviedes |
| 2004/0258285 A1 | 12/2004 | Hansen et al. |
| 2005/0203348 A1 | 9/2005 | Shihadeh et al. |
| 2007/0116328 A1 | 5/2007 | Sablak et al. |
| 2008/0001735 A1 | 1/2008 | Tran |
| 2008/0108880 A1 | 5/2008 | Young et al. |
| 2008/0279420 A1 | 11/2008 | Masticola et al. |
| 2008/0295837 A1 | 12/2008 | McCormick et al. |
| 2009/0024012 A1 | 1/2009 | Li et al. |
| 2009/0304280 A1 | 12/2009 | Aharoni et al. |
| 2010/0210924 A1 | 8/2010 | Parthasarathy et al. |
| 2010/0023655 A1 | 9/2010 | Jafari et al. |
| 2010/0236553 A1 | 9/2010 | Jafari et al. |
| 2010/0249630 A1 | 9/2010 | Droitcour et al. |
| 2010/0324437 A1 | 12/2010 | Freeman et al. |
| 2011/0144517 A1 | 6/2011 | Cervantes |
| 2011/0150274 A1 | 6/2011 | Patwardhan et al. |
| 2012/0075464 A1 | 3/2012 | Derenn |
| 2012/0065533 A1 | 5/2012 | Carrillo, Jr. et al. |
| 2012/0243797 A1 | 9/2012 | Di Venuto Dayer et al. |
| 2013/0267873 A1 | 10/2013 | Fuchs |
| 2013/0271591 A1 | 10/2013 | Van Leest et al. |
| 2013/0272393 A1 | 10/2013 | Kirenko et al. |
| 2013/0275873 A1 | 10/2013 | Shaw et al. |
| 2013/0324830 A1 | 12/2013 | Bernal et al. |
| 2013/0324876 A1 | 12/2013 | Bernal et al. |
| 2014/0023235 A1 | 1/2014 | Cennini et al. |
| 2014/0052006 A1 | 2/2014 | Lee et al. |
| 2014/0053840 A1 | 2/2014 | Liu |
| 2014/0139405 A1 | 5/2014 | Ribble et al. |
| 2014/0140592 A1 | 5/2014 | Lasenby et al. |
| 2014/0235976 A1 | 8/2014 | Bresch et al. |
| 2014/0267718 A1 | 9/2014 | Govro et al. |
| 2014/0272860 A1 | 9/2014 | Peterson et al. |
| 2014/0275832 A1 | 9/2014 | Muehlsteff et al. |
| 2014/0276104 A1 | 9/2014 | Tao et al. |
| 2014/0330336 A1 | 11/2014 | Errico et al. |
| 2014/0334697 A1 | 11/2014 | Kersten et al. |
| 2014/0358017 A1 | 12/2014 | Op Den Buijs et al. |
| 2014/0378810 A1 | 12/2014 | Davis et al. |
| 2014/0379369 A1 | 12/2014 | Kokovidis et al. |
| 2015/0003723 A1 | 1/2015 | Huang et al. |
| 2015/0094597 A1 | 4/2015 | Mestha et al. |
| 2015/0131880 A1 | 5/2015 | Wang et al. |
| 2015/0157269 A1 | 6/2015 | Lisogurski et al. |
| 2015/0223731 A1 | 8/2015 | Sahin |
| 2015/0238150 A1 | 8/2015 | Subramaniam |
| 2015/0265187 A1 | 9/2015 | Bernal et al. |
| 2015/0282724 A1 | 10/2015 | McDuff et al. |
| 2015/0301590 A1 | 10/2015 | Furst et al. |
| 2015/0317814 A1 | 11/2015 | Johnston et al. |
| 2016/0000335 A1 | 1/2016 | Khachaturian et al. |
| 2016/0049094 A1 | 2/2016 | Gupta et al. |
| 2016/0082222 A1 | 3/2016 | Garcia et al. |
| 2016/0140828 A1 | 5/2016 | Deforest |
| 2016/0143598 A1 | 5/2016 | Rusin et al. |
| 2016/0151022 A1 | 6/2016 | Berlin et al. |
| 2016/0156835 A1 | 6/2016 | Ogasawara et al. |
| 2016/0174887 A1 | 6/2016 | Kirenko et al. |
| 2016/0210747 A1 | 7/2016 | Hay et al. |
| 2016/0235344 A1 * | 8/2016 | Auerbach ............. A61B 5/1117 |
| 2016/0310084 A1 | 10/2016 | Banerjee et al. |
| 2016/0317041 A1 | 11/2016 | Porges et al. |
| 2016/0345931 A1 | 12/2016 | Xu et al. |
| 2016/0367186 A1 | 12/2016 | Freeman et al. |
| 2017/0007342 A1 | 1/2017 | Kasai et al. |
| 2017/0007795 A1 | 1/2017 | Pedro et al. |
| 2017/0055877 A1 | 3/2017 | Niemeyer |
| 2017/0065484 A1 | 3/2017 | Addison et al. |
| 2017/0071516 A1 | 3/2017 | Bhagat et al. |
| 2017/0095215 A1 | 4/2017 | Watson et al. |
| 2017/0095217 A1 | 4/2017 | Hubert et al. |
| 2017/0119340 A1 | 5/2017 | Nakai et al. |
| 2017/0147772 A1 | 5/2017 | Meehan et al. |
| 2017/0164904 A1 | 6/2017 | Kirenko |
| 2017/0172434 A1 | 6/2017 | Amelard et al. |
| 2017/0173262 A1 | 6/2017 | Veltz |
| 2017/0238805 A1 | 8/2017 | Addison et al. |
| 2017/0238842 A1 | 8/2017 | Jacquel et al. |
| 2017/0311887 A1 | 11/2017 | Leussler et al. |
| 2017/0319114 A1 | 11/2017 | Kaestle |
| 2018/0042486 A1 | 2/2018 | Yoshizawa et al. |
| 2018/0042500 A1 | 2/2018 | Liao et al. |
| 2018/0049669 A1 * | 2/2018 | Vu ....................... A61B 5/0507 |
| 2018/0053392 A1 | 2/2018 | White et al. |
| 2018/0104426 A1 | 4/2018 | Oldfield et al. |
| 2018/0106897 A1 | 4/2018 | Shouldice et al. |
| 2018/0169361 A1 | 6/2018 | Dennis et al. |
| 2018/0217660 A1 | 8/2018 | Dayal et al. |
| 2018/0228381 A1 | 8/2018 | LeBoeuf et al. |
| 2018/0310844 A1 | 11/2018 | Tezuka et al. |
| 2018/0325420 A1 | 11/2018 | Gigi |
| 2018/0333050 A1 | 11/2018 | Greiner et al. |
| 2019/0050985 A1 | 2/2019 | Den Brinker et al. |
| 2019/0133499 A1 | 5/2019 | Auerbach |
| 2019/0142274 A1 | 5/2019 | Addison et al. |
| 2019/0199970 A1 | 6/2019 | Greiner et al. |

(56) References Cited

U.S. PATENT DOCUMENTS

| | | |
|---|---|---|
| 2019/0209046 A1 | 7/2019 | Addison et al. |
| 2019/0209083 A1 | 7/2019 | Wu et al. |
| 2019/0307365 A1 | 10/2019 | Addison et al. |
| 2019/0311101 A1 | 10/2019 | Nienhouse |
| 2019/0343480 A1 | 11/2019 | Shute et al. |
| 2019/0380599 A1 | 12/2019 | Addison et al. |
| 2019/0380807 A1 | 12/2019 | Addison et al. |
| 2020/0046302 A1 | 2/2020 | Jacquel et al. |
| 2020/0187827 A1 | 6/2020 | Addison et al. |
| 2020/0202154 A1 | 6/2020 | Wang et al. |
| 2020/0205734 A1 | 7/2020 | Mulligan et al. |
| 2020/0237225 A1 | 7/2020 | Addison et al. |
| 2020/0242790 A1 | 7/2020 | Addison et al. |
| 2020/0250406 A1 | 8/2020 | Wang et al. |
| 2020/0253560 A1 | 8/2020 | De Haan |
| 2020/0289024 A1 | 9/2020 | Addison et al. |
| 2020/0329976 A1 | 10/2020 | Chen et al. |
| 2021/0068670 A1 | 3/2021 | Redtel |
| 2021/0153746 A1 | 5/2021 | Addison et al. |
| 2021/0235992 A1 | 8/2021 | Addison |

FOREIGN PATENT DOCUMENTS

| | | | |
|---|---|---|---|
| CN | 112233813 A | 1/2021 | |
| DE | 19741982 A1 | 10/1998 | |
| EP | 2428162 A1 | 3/2012 | |
| EP | 2772828 A1 | 9/2014 | |
| EP | 2793189 A2 | 10/2014 | |
| EP | 3207862 | 8/2017 | |
| EP | 3207863 | 8/2017 | |
| EP | 3384827 | 10/2018 | |
| JP | 2009544080 A | 12/2009 | |
| JP | 2011130996 A | 7/2011 | |
| KR | 101644843 B1 | 8/2016 | |
| RU | RS 20120373 A1 * | 4/2014 | |
| WO | 2004100067 A2 | 11/2004 | |
| WO | 2010034107 A1 | 4/2010 | |
| WO | 2010036653 A1 | 4/2010 | |
| WO | WO2015059700 | 4/2015 | |
| WO | 2015078735 A1 | 6/2015 | |
| WO | 2015110859 A1 | 7/2015 | |
| WO | 2016065411 A1 | 5/2016 | |
| WO | 2016178141 A1 | 11/2016 | |
| WO | 2016209491 A1 | 12/2016 | |
| WO | WO2017/060463 | 4/2017 | |
| WO | WO2017/089139 | 6/2017 | |
| WO | WO-2017100188 A2 * | 6/2017 | A61B 5/0024 |
| WO | 2017144934 A1 | 8/2017 | |
| WO | 2018042376 A1 | 3/2018 | |
| WO | 2019094893 A1 | 5/2019 | |
| WO | 2019135877 A1 | 7/2019 | |
| WO | 2019240991 A1 | 12/2019 | |
| WO | 2020033613 A1 | 2/2020 | |
| WO | 2021044240 A1 | 3/2021 | |

OTHER PUBLICATIONS

Bartula M, Tigges T, Muehlsteff J. Camera-based system for contactless monitoring of respiration. In2013 35th Annual International Conference of the IEEE Engineering in Medicine and Biology Society (EMBC) Jul. 3, 2013 (pp. 2672-2675). IEEE.*

Reyes BA, Reljin N, Kong Y, Nam Y, Chon KH. Tidal volume and instantaneous respiration rate estimation using a volumetric surrogate signal acquired via a smartphone camera. IEEE journal of biomedical and health informatics. Feb. 25, 2016;21(3):764-77.*

Li MH, Yadollahi A, Taati B. A non-contact vision-based system for respiratory rate estimation. In2014 36th Annual International Conference of the IEEE Engineering in Medicine and Biology Society Aug. 26, 2014 (pp. 2119-2122). IEEE.*

Transue S, Nguyen P, Vu T, Choi MH. Real-time tidal volume estimation using iso-surface reconstruction. In2016 IEEE First International Conference on Connected Health: Applications, Systems and Engineering Technologies (CHASE) Jun. 27, 2016 (pp. 209-218). IEEE.*

Harte JM, Golby CK, Acosta J, Nash EF, Kiraci E, Williams MA, Arvanitis TN, Naidu B. Chest wall motion analysis in healthy volunteers and adults with cystic fibrosis using a novel Kinect-based motion tracking system. Medical & biological engineering & computing. Nov. 2016;54(11):1631-40.*

Al-Naji A, Gibson K, Lee SH, Chahl J. Real time apnoea monitoring of children using the Microsoft Kinect sensor: a pilot study. Sensors. Feb. 3, 2017;17(2):286.*

International Search Report and Written Opinion for International Application No. PCT/US2018/065492, dated Mar. 8, 2019, 12 pages.

Armanian, A. M., "Caffeine administration to prevent apnea in very premature infants", Pediatrics & Neonatology, 57 (5), 2016, pp. 408-412, 5 pages.

Di Fiore, J.M., et al., "Intermittent hypoxemia and oxidative stress in preterm infants", Respiratory Physiology & Neurobiology, No. 266, 2019, pp. 121-129, 25 pages.

Grimm, T., et al., "Sleep position classification from a depth camera using bed aligned maps", 23rd International Conference on Pattern Recognition (ICPR), Dec. 2016, pp. 319-324, 6 pages.

Liu, S., et al., "In-bed pose estimation: Deep learning with shallow dataset. IEEE journal of translational engineering in health and medicine", IEEE Journal of Translational Engineering in Health and Medicine, No. 7, 2019, pp. 1-12, 12 pages.

Wulbrand, H., et al., "Submental and diaphragmatic muscle activity during and at resolution of mixed and obstructive apneas and cardiorespiratory arousal in preterm infants", Pediatric Research, No. 38(3), 1995, pp. 298-305, 9 pages.

Aarts, Lonneke A.M. et al. "Non-contact heart rate monitoring utilizing camera photoplethysmography in the neonatal intensive care unit—A pilot study", Early Human Development 89, 2013, pp. 943-948.

Abbas A. K. et al., "Neonatal non-contact respiratory monitoring based on real-time infrared thermography," Biomed. Eng. Online, vol. 10, No. 93, 2011, 17 pages.

Addison, P. S. et al., "Video-based Heart Rate Monitoring across a Range of Skin Pigmentations during an Acute Hypoxic Challenge," J Clin Monit Comput, Nov. 9, 2017, 10 pages.

Addison, Paul S. PhD, "A Review of Signal Processing Used in the Implementation of the Pulse Oximetry Phtoplethysmographic Fluid Responsiveness Parameter", International Anesthesia Research Society, Dec. 2014, vol. 119, No. 6, pp. 1293-1306.

Addison, Paul S., et al., "Developing an algorithm for pulse oximetry derived respiratory rate (RRoxi): a healthy volunteer study", J Clin Monit Comput (2012) 26, pp. 45-51.

Addison,Paul S., et al., "Pulse oximetry-derived respiratory rate in general care floor patients", J Clin Monit Comput, 2015, 29, pp. 113-120.

Bhattacharya, S. et al., "A Novel Classification Method for Predicting Acute Hypotensive Episodes in Critical Care," 5th ACM Conference on Bioinformatics, Computational Biology and Health Informatics (ACM-BCB 2014), Newport Beach, USA, 2014, 10 pages.

Bhattacharya, S. et al., "Unsupervised learning using Gaussian Mixture Copula models," 21st International Conference on Computational Statistics (COMPSTAT 2014), Geneva, Switzerland, 2014, 8 pages.

Bickler, Philip E. et al., "Factors Affecting the Performance of 5 Cerebral Oximeters During Hypoxia in Healthy Volunteers", Society for Technology in Anesthesia, Oct. 2013, vol. 117, No. 4, pp. 813-823.

Bousefsaf, Frederic, et al., "Continuous wavelet filtering on webcam photoplethysmographic signals to remotely assess the instantaneous heart rate", Biomedical Signal Processing and Control 8, 2013, pp. 568-574.

Bruser, C. et al., "Adaptive Beat-to-Beat Heart Rate Estimation in Ballistocardiograms," IEEE Transactions Information Technology in Biomedicine, vol. 15, No. 5, Sep. 2011, pp. 778-786.

(56) References Cited

OTHER PUBLICATIONS

BSI Standards Publication, "Medical electrical equipment, Part 2-61: Particular requirements for basic safety and essential performance of pulse oximeter equipment", BS EN ISO 80601-2-61:2011, 98 pages.
Cennini, Giovanni, et al., "Heart rate monitoring via remote phtoplethysmography with motion artifacts reduction", Optics Express, Mar. 1, 2010, vol. 18, No. 5, pp. 4867-4875.
Colantonio, S. "A smart mirror to promote a healthy lifestyle," Biosystems Engineering, vol. 138, Oct. 2015, pp. 33-43, Innovations in Medicine and Healthcare.
Cooley et al. "An Algorithm for the Machine Calculation of Complex Fourier Series," Aug. 17, 1964, pp. 297-301.
European Search Report; European Patent Application No. 17156334.9; Applicant: Covidien LP; dated Jul. 13, 2017, 10 pgs.
European Search Report; European Patent Application No. 17156337.2; Applicant: Covidien LP; dated Jul. 13, 2017, 10 pgs.
Fei J. et al., "Thermistor at a distance: unobtrusive measurement of breathing," IEEE Transactions on Biomedical Engineering, vol. 57, No. 4, pp. 988-998, 2010.
George et al., "Respiratory Rate Measurement From PPG Signal Using Smart Fusion Technique," International Conference on Engineering Trends and Science & Humanities (ICETSH-2015), 5 pages, 2015.
Goldman, L. J., "Nasal airflow and thoracoabdominal motion in children using infrared thermographic video processing," Pediatric Pulmonology, vol. 47, No. 5, pp. 476-486, 2012.
Guazzi, Alessandro R., et al., "Non-contact measurement of oxygen saturation with an RGB camera," Biomedical Optics Express, Sep. 1, 2015, vol. 6, No. 9, pp. 3320-3338.
Han, J. et al., "Visible and infrared image registration in man-made environments employing hybrid visual features," Pattern Recognition Letters, vol. 34, No. 1, pp. 42-51, 2013.
Huddar, V. et al. "Predicting Postoperative Acute Respiratory Failure in Critical Care using Nursing Notes and Physiological Signals," 36th Annual Intl Conf of IEEE Engineering in Medicine and Biology Society IEEE EMBC2014, Chicago, 2014, pp. 2702-2705.
Javadi M. et al., Diagnosing Pneumonia in Rural Thailand: "Digital Cameras versus Film Digitizers For Chest Radiograph Teleradiology," International Journal of Infectious Disease, Mar. 2006;10(2), pp. 129-135.
Jopling, Michael W., et al., "Issues in the Laboratory Evaluation of Pulse Oximeter Performance", Anesth. Analg. 2002; 94, pp. S62-S68.
Kastle, Siegfried W., et al., "Determining the Artifact Sensitivity of Recent Pulse Oximeters During Laboratory Benchmarking", Journal of Clinical Monitoring and Computing, vol. 16, No. 7, 2000, pp. 509-522.
Klaessens J. H. G. M. et al., "Non-invasive skin oxygenation imaging using a multi-spectral camera system: Effectiveness of various concentration algorithms applied on human skin," Proc. Of SPIE vol. 7174 717408-1, 2009, 14 pages.
Kong, Lingqin, et al., "Non-contact detection of oxygen saturation based on visible light imaging device using ambient light", Optics Express, Jul. 29, 2013, vol. 21, No. 15, pp. 17464-17471.
Kortelainen, J. et al., "Sleep staging based on signals acquired through bed sensor," IEEE Transactions on Information Technology in Biomedicine, vol. 14, No. 3, pp. 776-785, May 2010.
Kumar, M. et al., "Distance PPG: Robust non-contact vital signs monitoring using a camera," Biomedical optics express 2015, 24 pages.
Kwon, Sungjun, et al., "Validation of heart rate extraction using video imaging on a built-in camera system of a smartphone", 34th Annual International Conference of the IEEE EMBS, San Diego, CA, USA, Aug. 28-Sep. 1, 2012, pp. 2174-2177.
Lai, C. J. et al. "Heated humidified high-flow nasal oxygen prevents intraoperative body temperature decrease in non-intubated thoracoscopy." Journal of Anesthesia. Oct. 15, 2018. 8 pages.
Li et al., "A Non-Contact Vision-Based System for Respiratory Rate Estimation", 978-1-4244-7929-0/14, 2014, 4 pages.
Liu H. et al., "A Novel Method Based on Two Cameras For Accurate Estimation of Arterial Oxygen Saturation," BioMedical Engineering OnLine, 2015, 17 pages.
Liu, C. et al., "Motion magnification" ACM Transactions on Graphics (TOG), vol. 24, No. 3, pp. 519-526, 2005.
Lv, et al., "Class Energy Image Analysis for Video Sensor-Based Gait Recognition: A Review", Sensors 2015, 15, pp. 932-964.
McDuff, Daniel J., et al., "A Survey of Remote Optical Photoplethysmographic Imaging Methods", 978-1-4244-9270-1/15, IEEE, 2015, pp. 6398-6404.
Mestha, L.K. et al., "Towards Continuous Monitoring of Pulse Rate in Neonatal Intensive Care Unit with a Webcam" in Proc. of 36th Annual Int. Conf. of the IEEE Engineering in Medicine and Biology Society, Chicago, Il pp. 1-5, 2014.
Pereira, C. et al. "Noncontact Monitoring of Respiratory Rate in Newborn Infants Using Thermal Imaging." IEEE Transactions on Biomedical Engineering. Aug. 23, 2018. 10 pages.
Poh et al., "Non-contact, automated cardiac pulse measurements using video imaging and blind source separation," Opt. Express 18,10762-10774 (2010), 14 pages.
Poh, et al., "Advancements in Noncontact, Multiparameter Physiological Measurements Using a Webcam", IEEE Transactions on Biomedical Engineering, vol. 58, No. 1, Jan. 2011, 5 pages.
Rajan, V. et al., "Clinical Decision Support for Stroke using Multiview Learning based Models for NIHSS Scores," PAKDD 2016 Workshop: Predictive Analytics in Critical Care (PACC), Auckland, New Zealand, 10 pages.
Rajan, V. et al., "Dependency Clustering of Mixed Data with Gaussian Mixture Copulas," 25th International Joint Conference on Artificial Intelligence IJCAI 2016, New York, USA, 7 pages.
Reisner, A. et al., "Utility of the Photoplethysmogram in Circulatory Monitoring". American Society of Anesthesiologist, May 2008, pp. 950-958.
Rougier, Caroline, et al., "Robust Video Surveillance for Fall Detection Based on Human Shape Deformation", IEEE Transactions on Circuits and Systems for Video Technology, vol. 21, No. 5, May 2011, pp. 611-622.
Rubinstein, M., "Analysis and Visualization of Temporal Variations in Video", Department of Electrical Engineering and Computer Science, Massachusetts Institute of Technology, Feb. 2014, 118 pages.
Scalise, Lorenzo, et al., "Heart rate measurement in neonatal patients using a web camera.", 978-1-4673-0882-3/12, IEEE, 2012, 4 pages.
Sengupta, A. et al., "A Statistical Model for Stroke Outcome Prediction and Treatment Planning," 38th Annual International Conference of the IEEE Engineering in Medicine and Biology (Society IEEE EMBC 2016), Orlando, USA,2016, 4 pages.
Shah, Nitin, et al., "Performance of three new-generation pulse oximeters during motion and low perfusion in volunteers", Journal of Clinical Anesthesia, 2012, 24, pp. 385-391.
Shao, Dangdang, et al., "Noncontact Monitoring Breathing Pattern, Exhalation Flow Rate and Pulse Transit Time", IEEE Transactions on Biomedical Engineering, vol. 61, No. 11, Nov. 2014, pp. 2760-2767.
Shrivastava, H. et al., "Classification with Imbalance: A Similarity-based Method for Predicting Respiratory Failure," 2015 IEEE International Conference on Bioinformatics and Biomedicine (IEEE BIBM2015), Washington DC, USA, 8 pages.
Sun, Yu, et al., "Noncontact imaging phtoplethysmography to effectively access pulse rate variability", Journal of Biomedical Optics, Jun. 2013, vol. 18(6), 10 pages.
Tamura et al., "Wearable Photoplethysmographic Sensors—Past & Present," Electronics, 2014, pp. 282-302.
Tarassenko, L., et al., "Non-contact video-based vital sign monitoring using ambient light and auto-regressive models", Institute of Physics and Engineering in Medicine, 2014, pp. 807-831.
Teichmann, D. et al., "Non-contact monitoring techniques—Principles and applications," in Proc. of IEEE International Conference of the Engineering in Medicine and Biology Society (EMBC), San Diego, CA, 2012, 4 pages.
Verkruysse, Wim, et al., "Calibration of Contactless Pulse Oximetry", Anesthesia & Analgesia, Jan. 2017, vol. 124, No. 1, pp. 136-145.

(56) References Cited

OTHER PUBLICATIONS

Villarroel, Mauricio, et al., "Continuous non-contact vital sign monitoring in neonatal intensive care unit", Healthcare Technology Letters, 2014, vol. 1, Issue 3, pp. 87-91.
Wadhwa, N. et al., "Phase-Based Video Motion Processing," MIT Computer Science and Artificial Intelligence Lab, Jul. 2013, 9 pages.
Wadhwa, N. et al., "Riesz pyramids for fast phase-based video magnification." in Proc. of IEEE International Conference on Computational Photography (ICCP), Santa Clara, CA, pp. 1-10, 2014.
Wang, W. et al., "Exploiting spatial redundancy of image sensor for motion robust rPPG." IEEE Transactions on Biomedical Engineering, vol. 62, No. 2, pp. 415-425, 2015.
Wu, H.Y. et al., "Eulerian video magnification for revealing subtle changes in the world," ACM Transactions on Graphics (TOG), vol. 31, No. 4, pp. 651-658, 2012.
Yu Sun et al. "Motion-compensated noncontact imaging photoplethysmography to monitor cardiorespiratory status during exercise," Journal of Biomedical Optics, vol. 16, No. 7, Jan. 1, 2011, 10 pages.
Zhou, J. et al., "Maximum parsimony analysis of gene copy number changes in tumor phylogenetics," 15th International Workshop on Algorithms in Bioinformatics WABI 2015, Atlanta, USA, 13 pages.
Ni et al. "RGBD-Camera Based Get-Up Event Detection for Hospital Fall Prevention." Acoustics, Speech and Signal Processing (ICASSP). 2012 IEEE International Conf., Mar. 2012: pp. 1405-1408.
Amazon, "Dockem Koala Tablet Wall Mount Dock for iPad Air/Mini/Pro, Samsung Galaxy Tab/Note, Nexus 7/10, and More (Black Brackets, Screw-in Version)", https://www.amazon.com/Tablet-Dockem-Samsung-Brackets-Version-dp/B00JV75FC6?th=1, First available Apr. 22, 2014, viewed on Nov. 16, 2021, Apr. 22, 2014, 4 pages.
Gsmarena, "Apple iPad Pro 11 (2018)", https://www.gsmarena.com/apple_ipad_pro_11_(2018)-9386.pjp, viewed on Nov. 16, 2021, 1 page.
Hyvarinen, A. et al., "Independent Component Analysis: Algorithms and Applications", Neural Networks, vol. 13, No. 4, 2000, pp. 411-430, 31 pages.
International Search Report and Written Opinion for International Application No. PCT/US19/035433, dated Nov. 11, 2019, 17 pages.
International Application No. PCT/US2019/035433 Invitation to Pay Additional Fees and Partial International Search Report dated Sep. 13, 2019, 16 pages (MD60009PCT).
International Application No. PCT/US2019/045600 International Search Report and Written Opinion dated Oct. 23, 2019, 19 pages (MD60002PCT).
Litong Feng, et al. Dynamic ROI based on K-means for remote photoplethysmography, IEEE International Conference on Accoustics, Speech and Signal Processing (ICASSP), Apr. 2015, p. 1310-1314 (Year 2015) (5 pp.).
Nguyen, et al., "3D shape, deformation and vibration measurements using infrared Kinect sensors and digital image correlation", Applied Optics, vol. 56, No. 32, Nov. 8, 2017, 8 pages.
Povsi, et al., Real-Time 3D visualization of the thoraco-abdominal surface during breathing with body movement and deformation extraction, Physiological Measurement, vol. 36, No. 7, May 28, 2015, pp. 1497-1516.
Prochazka et al., "Microsoft Kinect Visual and Depth Sensors for Breathing and Heart Rate Analysis", Sensors, vol. 16, No. 7, Jun. 28, 2016, 11 pages.
Schaerer, et al., "Multi-dimensional respiratory motion tracking from markerless optical surface imaging based on deformable mesh registration", Physics in Medicine and Biology, vol. 57, No. 2, Dec. 14, 2011, 18 pages.
Zaunseder, et al. "Spatio-temporal analysis of blood perfusion by imaging photoplethysmography," Progress in Biomedical Optics and Imaging, SPIE—International Society for Optical Engineering, vol. 10501, Feb. 20, 2018, 15 pages.
Amelard, et al., "Non-contact transmittance photoplethysmographic imaging (PPGI) for long-distance cardiovascular monitoring," ResearchGate, Mar. 23, 2015, pp. 1-13, XP055542534 [Retrieved online Jan. 15, 2019].
Nisar, et al. "Contactless heart rate monitor for multiple persons in a video", IEEE International Conference on Consumer Electronics—Taiwan (ICCE-TW), May 27, 2016, pp. 1-2, XP032931229 [Retrieved on Jul. 25, 2016].
International Search Report and Written Opinion for International Application No. PCT/US2018/060648, dated Jan. 28, 2019, 17 pages.
Barone, et al., "Computer-aided modelling of three-dimensional maxillofacial tissues through multi-modal imaging", Journal of Engineering in Medicine, Part H. vol. 227, No. 2, Feb. 1, 2013, pp. 89-104.
Barone, et al., "Creation of 3D Multi-body Orthodontic Models by Using Independent Imaging Sensors", Senros MDPI AG Switzerland, vol. 13, No. 2, Jan. 1, 2013, pp. 2033-2050.
"International Search Report and Written Opinion", International Application No. PCT/US2021/015669, dated Apr. 12, 2021, 15 pages.
Fischer, et al., "ReMoteCare: Health Monitoring with Streaming Video", OCMB '08, 7th International Conference on Mobile Business, IEEE, Piscataway, NJ,, Jul. 7, 2008, pp. 280-286.
Lawrence, E., et al., "Data Collection, Correlation and Dissemination of Medical Sensor information in a WSN", IEEE 2009 Fifth International Conference on Networking and Services, 978-0-7695-3586-9/09, Apr. 20, 2009, pp. 402-408, 7 pages.
Mukherjee, S., et al., "Patient health management system using e-health monitoring architecture", IEEE, International Advance Computing Conference (IACC), 978-1-4799-2572-8/14, Feb. 21, 2014, pp. 400-405, 6 pages.
Srinivas, J., et al., "A Mutual Authentication Framework for Wireless Medical Sensor Networks", Journal of Medical Systems, 41:80, 2017, pp. 1-19, 19 pages.

\* cited by examiner

SYSTEMS AND METHODS FOR VIDEO-BASED NON-CONTACT TIDAL VOLUME MONITORING

CROSS-REFERENCE TO RELATED APPLICATION(S)

The present application claims priority to U.S. Provisional Patent Application No. 62/614,763, filed Jan. 8, 2018, the disclosure of which is incorporated herein by reference in its entirety.

BACKGROUND

Many conventional medical monitors require attachment of a sensor to a patient in order to detect physiologic signals from the patient and transmit detected signals through a cable to the monitor. These monitors process the received signals and determine vital signs such as the patient's pulse rate, respiration rate, and arterial oxygen saturation. For example, a pulse oximeter is a finger sensor that may include two light emitters and a photodetector. The sensor emits light into the patient's finger and transmits the detected light signal to a monitor. The monitor includes a processor that processes the signal, determines vital signs (e.g., pulse rate, respiration rate, arterial oxygen saturation), and displays the vital signs on a display.

Other monitoring systems include other types of monitors and sensors, such as electroencephalogram (EEG) sensors, blood pressure cuffs, temperature probes, air flow measurement devices (e.g., spirometer), and others. Some wireless, wearable sensors have been developed, such as wireless EEG patches and wireless pulse oximetry sensors.

Video-based monitoring is a new field of patient monitoring that uses a remote video camera to detect physical attributes of the patient. This type of monitoring may also be called "non-contact" monitoring in reference to the remote video sensor, which does not contact the patient. The remainder of this disclosure offers solutions and improvements in this new field.

SUMMARY

In an embodiment described herein, a method of determining tidal volume of a patient, includes receiving, by a processor, at least one image including depth information for at least part of the patient. The method further includes determining, by the processor, a reference point on the patient. The method further includes determining, by the processor, a region of interest based at least in part on the reference point. The region of interest corresponds to a trunk area of the patient. The method further includes monitoring changes in the depth information in the region of interest over time. The method further includes mapping the monitored changes in depth information to a tidal volume for the patient.

In some embodiments, the region of interest is further defined based on at least one body coordinate determined from the reference point.

In some embodiments, each of the at least one body coordinates correspond to a location on a body of the patient, and the location on the body of the at least one body coordinate is at least one of a shoulder, a hip, a neck, a chest, and a waist.

In some embodiments, the region of interest is further determined based on a distance of various portions of the patient from a camera that captures the at least one image.

In some embodiments, the region of interest is further determined by discarding various portions of a flood fill in response to determining that the patient is rotated such that the patient is not orthogonal to a line of sight of a camera that captures the at least one image.

In some embodiments, the region of interest is further determined by determining that the trunk area of the patient is partially obscured and excluding a partially obscured region from the region of interest.

In some embodiments, the at least one image is captured by a first camera, and at least a second image comprising at least part of the patient is captured by a second camera.

In some embodiments, the method further includes determining, by the processor, a second region of interest of the patient based on at least the second image.

In some embodiments, the method further includes determining, by the processor, a second region of interest of the patient from the at least one image.

In some embodiments, the region of interest is a different size than the second region of interest.

In another embodiment described herein, a video-based method of monitoring a patient includes receiving, by a processor, a video feed including a plurality of images captured at different times. At least a portion of a patient is captured by the video feed. The method further includes determining, by the processor, a region of interest of the human patient on the video feed. The region of interest corresponds to a trunk area of the patient. The method further includes measuring, by the processor, changes to the region of interest over time. The method further includes determining, by the processor, based on the changes to the region of interest, a tidal volume of the patient.

In some embodiments, the method further includes comparing, by the processor, the tidal volume determined based on the changes to the region of interest to an output of an air flow measurement device and calibrating, by the processor, the tidal volume determination based on the comparison.

In some embodiments, the method further includes receiving, by the processor, demographic information about the patient and adjusting the tidal volume determination based on the demographic information.

In some embodiments, the demographic information comprises at least one of a sex, height, weight, body mass index (BMI), and age of the patient.

In some embodiments, a size of the region of interest is at least partially dependent on a distance of the patient from a camera that captures the video feed.

In some embodiments, the method further includes determining, using the processor, a change in the tidal volume of the patient over time.

In some embodiments, the method further includes determining, using the processor, based on the change in the tidal volume of the patient, a potential hypoventilation condition.

In some embodiments, the region of interest is configured based on an orientation of the patient with respect to a camera that captures the video feed.

In some embodiments, the tidal volume of the patient is determined based on an orientation of the patient with respect to a camera that captures the video feed.

In some embodiments, the video feed is captured by a first camera, and a second video feed is captured by a second camera, and at least a second portion of the patient is captured by the second video feed.

In some embodiments, the method further includes determining, by the processor, a second region of interest of the patient based on the second video feed.

In some embodiments, the tidal volume is further determined based on changes to the second region of interest over time.

In some embodiments, the method further includes determining, by the processor, a second region of interest of the patient from the video feed.

In some embodiments, the region of interest is a different size than the second region of interest.

In some embodiments, the tidal volume is further determined based on changes to the second region of interest over time.

In a further aspect, which may be provided independently, there is provided an apparatus for determining tidal volume of a patient, the apparatus comprising a processor configured to: receive at least one image comprising depth information for at least a portion of the patient; determine a reference point on the patient; determine a region of interest based at least in part on the reference point, wherein the region of interest corresponds to a trunk area of the patient; monitor changes in the depth information in the region of interest over time; and map the monitored changes in depth information to a tidal volume for the patient.

In a further aspect, which may be provided independently, there is provided an apparatus for video-based monitoring of a patient, the apparatus comprising a processor configured to: receive a video feed comprising a plurality of images captured at different times, wherein at least a portion of a patient is captured within the video feed; determine a region of interest of the patient on the video feed, wherein the region of interest corresponds to a trunk area of the patient; measure changes to the region of interest over time, and determine a tidal volume of the patient based on the changes to the region of interest.

DETAILED DESCRIPTION

Figure 1:
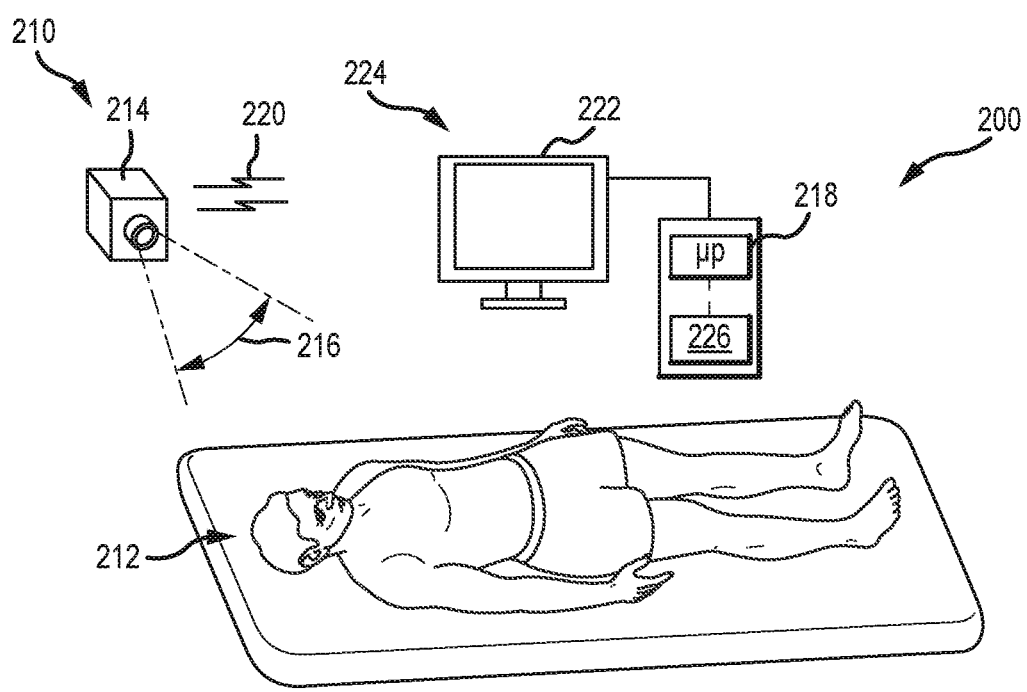
FIG. 1 is a schematic view of a video-based patient monitoring system according to various embodiments described herein.

The present invention relates to the field of medical monitoring, and in particular non-contact monitoring of patient with regard to respiratory monitoring. Systems, methods, and computer readable media are described herein for determining a region of interest of a patient and monitoring that region of interest to determine tidal volume of the patient. The systems, methods, and computer readable media disclosed herein have the potential to improve record-keeping, improve patient care, reduce errors in vital sign measurements, increase frequency and accuracy of respiratory monitoring, help healthcare providers better characterize and respond to adverse medical conditions indicated by decreased tidal volume (e.g., hypoventilation), and generally improve monitoring of patients, along with many other potential advantages discussed below. Tidal volume measurement/monitoring can further be helpful in the following areas: respiratory compromise, non-invasive ventilation, volume capnography, neonatal monitoring, pain management, post-surgery monitoring/treatment, and more. In particular, arterial blood oxygen saturation is a lagging indicator of respiratory compromise; it may take 60 seconds or longer for oxygen saturation levels to drop after a patient stops breathing. By monitoring breathing as disclosed herein, patients who have slow, shallow, or stopped breathing can be attended to more quickly, potentially saving lives and leading to better treatment.

Improvements disclosed herein can greatly increase the ability to detect or measure respiratory compromise, thereby increasing the level of care healthcare professionals can provide to patients. For example, the ability to determine the nature of respiration of a patient allows for the determination of progression of a disease state and/or impending complication including imminent respiratory arrest.

Beneficially, the systems, methods, and computer readable media disclosed herein provide for enhanced ways of measuring tidal volume of a patient using non-contact monitoring. With contact-based monitoring, tidal volume can be measured by utilizing an obtrusive mask incorporating a specialized flow measurement device. These masks and flow devices can be bulky and uncomfortable, and accordingly, this type of device may not be routinely used on patients. Additionally, even when it is used, it may not be used for long periods of time, and therefore may not be suitable for long term monitoring of tidal volume of a patient.

As described herein, non-contact video monitoring can be utilized to determine a volume of airflow indicative of tidal volume of a patient. For example, this may be accomplished using a depth sensing camera to monitor a patient and determine movements of their chest and/or other body parts as the patient breathes. This sensing of movement can be used to determine a tidal volume measurement. Accordingly, disclosed herein are systems, methods, and computer readable media for determining a tidal volume measurement using non-contact video monitoring of a patient. Furthermore, the systems, methods, and computer readable media disclosed herein accommodate patients with different characteristics and disease states, enabling more accurate patient-specific measurements across many different clinical scenarios.

FIG. 1 is a schematic view of a video-based patient monitoring system 200 and a patient 212 according to an embodiment of the invention. The system 200 includes a non-contact detector 210 placed remote from the patient 212. In this embodiment, the detector 210 includes a camera 214, such as a video camera. The camera 214 is remote from the patient, in that it is spaced apart from and does not contact the patient 212. The camera 214 includes a detector exposed to a field of view 216 that encompasses at least a portion of the patient 212.

The camera 214 generates a sequence of images over time. The camera 214 may be a depth sensing camera, such as a Kinect camera from Microsoft Corp. (Redmond, Wash.). A depth sensing camera can detect a distance between the camera and objects in its field of view. Such information can be used, as disclosed herein, to determine that a patient is within the field of view of the camera 214 and determine a region of interest (ROI) to monitor on the patient. Once an ROI is identified, that ROI can be monitored over time, and the change in depth of points within the ROI can represent movements of the patient associated with breathing. Accordingly, those movements, or changes of points within the ROI, can be used to determine tidal volume as disclosed herein.

In some embodiments, the system determines a skeleton outline of a patient to identify a point or points from which to extrapolate an ROI. For example, a skeleton may be used to find a center point of a chest, shoulder points, waist points, and/or any other points on a body. These points can be used to determine an ROI. For example, an ROI may be defined by filling in area around a center point of the chest. Certain determined points may define an outer edge of an ROI, such as shoulder points. In other embodiments, instead of using a skeleton, other points are used to establish an ROI. For example, a face may be recognized, and a chest area inferred in proportion and spatial relation to the face. In other embodiments as described herein, the system may establish the ROI around a point based on which parts are within a certain depth range of the point. In other words, once a point is determined that an ROI should be developed from, the system can utilize the depth information from a depth sensing camera to fill out the ROI as disclosed herein. For example, if a point on the chest is selected, depth information is utilized to determine an ROI area around the determined point that is a similar distance from the depth sensing camera as the determined point. This area is likely to be a chest. Using threshold depths in relation to a determined point is further shown and described below at least with respect to FIGS. 14 and 33-37.

In another example, a patient may wear a specially configured piece of clothing that identifies points on the body such as shoulders or the center of the chest. A system may identify those points by identifying the indicating feature of the clothing. Such identifying features could be a visually encoded message (e.g., bar code, QR code, etc.), or a brightly colored shape that contrasts with the rest of the patient's clothing, etc. In some embodiments, a piece of clothing worn by the patient may have a grid or other identifiable pattern on it to aid in recognition of the patient and/or their movement. In some embodiments, the identifying feature may be stuck on the clothing using a fastening mechanism such as adhesive, a pin, etc. For example, a small sticker may be placed on a patient's shoulders and/or center of the chest that can be easily identified from an image captured by a camera. In some embodiments, the indicator may be a sensor that can transmit a light or other information to a camera that enables its location to be identified in an image so as to help define an ROI. Therefore, different methods can be used to identify the patient and define an ROI.

In some embodiments, the system may receive a user input to identify a starting point for defining an ROI. For example, an image may be reproduced on an interface, allowing a user of the interface to select a patient for monitoring (which may be helpful where multiple humans are in view of a camera) and/or allowing the user to select a point on the patient from which the ROI can be determined (such as a point on the chest). Other methods for identifying a patient, points on the patient, and defining an ROI may also be used, as described further below.

In various embodiments, the ROI or portions of the ROI may be determined to move in accordance with respiratory patterns, to determine a tidal volume of the patient, as described further below.

Figure 2:
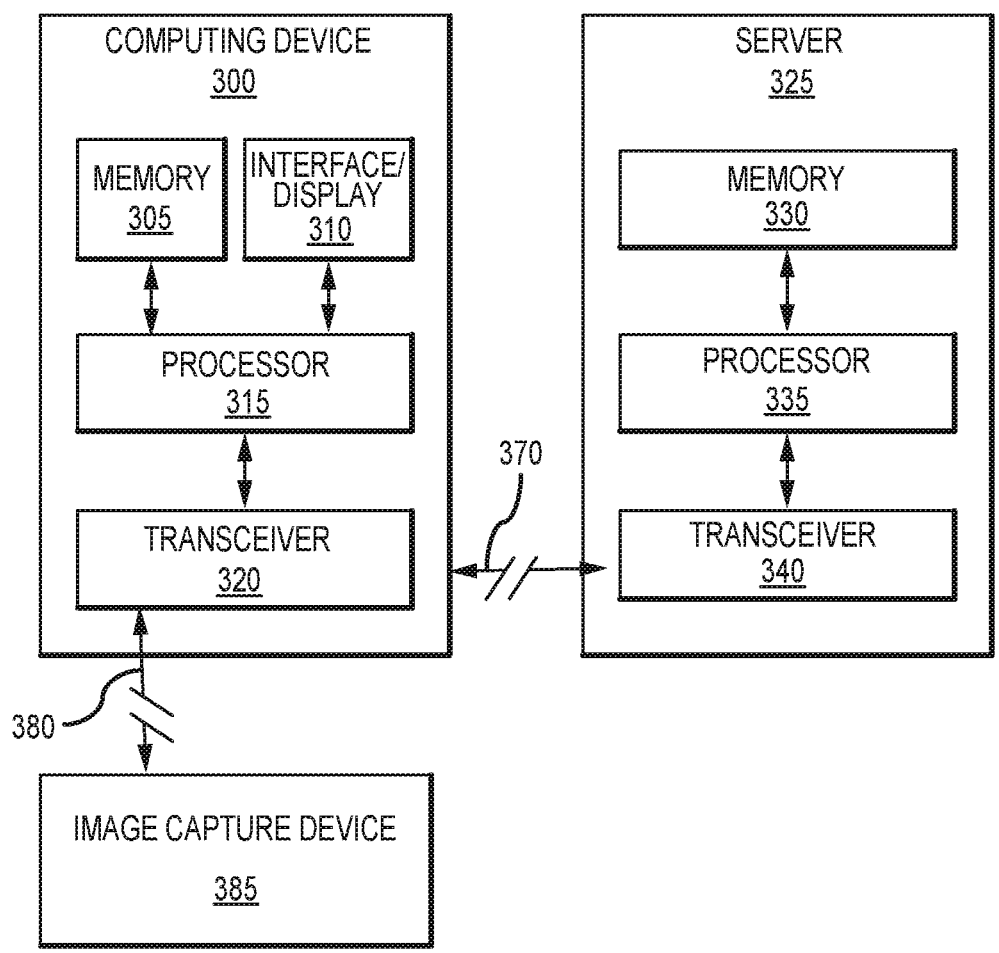
FIG. 2 is a block diagram illustrating a computing device, a server, and an image capture device according to various embodiments described herein.

The detected images are sent to a computing device through a wired or wireless connection 220. The computing device includes a processor 218, a display 222, and hardware memory 226 for storing software and computer instructions. Sequential image frames of the patient are recorded by the video camera 214 and sent to the processor 218 for analysis. The display 222 may be remote from the camera 214, such as a video screen positioned separately from the processor and memory. Other embodiments of the computing device may have different, fewer, or additional components than shown in FIG. 1. In some embodiments, the computing device may be a server. In other embodiments, the computing device of FIG. 1 may be additionally connected to a server (e.g., as shown in FIG. 2 and discussed below). The captured images/video can be processed or analyzed at the computing device and/or a server to determine tidal volume of the patient 212 as disclosed herein.

FIG. 2 is a block diagram illustrating a computing device 300, a server 325, and an image capture device 385 according to an embodiment of the invention. In various embodiments, fewer, additional and/or different components may be used in a system. The computing device 300 includes a processor 315 that is coupled to a memory 305. The processor 315 can store and recall data and applications in the memory 305, including applications that process information and send commands/signals according to any of the methods disclosed herein. The processor 315 may also display objects, applications, data, etc. on an interface/display 310. The processor 315 may also receive inputs through the interface/display 310. The processor 315 is also coupled to a transceiver 320. With this configuration, the processor 315, and subsequently the computing device 300, can communicate with other devices, such as the server 325 through a connection 370 and the image capture device 385 through a connection 380. For example, the computing device 300 may send to the server 325 information determined about a patient from images captured by the image capture device 385 (such as a camera), such as depth information of a patient in an image or tidal volume information determined about the patient, as disclosed herein. The computing device 300 may be the computing device of FIG. 1. Accordingly, the computing device 300 may be located remotely from the image capture device 385, or it may be local and close to the image capture device 385 (e.g., in the same room). In various embodiments disclosed herein, the processor 315 of the computing device 300 may perform the steps disclosed herein. In other embodiments, the steps may be performed on a processor 335 of the server 325. In some embodiments, the various steps and methods disclosed herein may be performed by both of the processors 315 and 335. In some embodiments, certain steps may be performed by the processor 315 while others are performed by the processor 335. In some embodiments, information determined by the processor 315 may be sent to the server 325 for storage and/or further processing.

In some embodiments, the image capture device 385 is a remote sensing device such as a video camera. In some embodiments, the image capture device 385 may be some other type of device, such as a proximity sensor or proximity sensor array, a heat or infrared sensor/camera, a sound/acoustic or radiowave emitter/detector, or any other device that may be used to monitor the location of a patient and an ROI of a patient to determine tidal volume. Body imaging technology may also be utilized to measure tidal volume according to the methods disclosed herein. For example, backscatter x-ray or millimeter wave scanning technology may be utilized to scan a patient, which can be used to define an ROI and monitor movement for tidal volume calculations. Advantageously, such technologies may be able to "see" through clothing, bedding, or other materials while giving an accurate representation of the patient's skin. This may allow for more accurate tidal wave measurements, particularly if the patient is wearing baggy clothing or is under bedding. The image capture device 385 can be described as local because it is relatively close in proximity to a patient so that at least a part of a patient is within the field of view of the image capture device 385. In some embodiments, the image capture device 385 can be adjustable to ensure that the patient is captured in the field of view. For example, the image capture device 385 may be physically movable, may have a changeable orientation (such as by rotating or panning), and/or may be capable of changing a focus, zoom, or other characteristic to allow the image capture device 385 to adequately capture a patient for ROI determination and tidal volume monitoring. In various embodiments, after an ROI is determined, a camera may focus on the ROI, zoom in on the ROI, center the ROI within a field of view by moving the camera, or otherwise may be adjusted to allow for better and/or more accurate tracking/measurement of the movement of a determined ROI.

The server 325 includes a processor 335 that is coupled to a memory 330. The processor 335 can store and recall data and applications in the memory 330. The processor 335 is also coupled to a transceiver 340. With this configuration, the processor 335, and subsequently the server 325, can communicate with other devices, such as the computing device 300 through the connection 370.

The devices shown in the illustrative embodiment may be utilized in various ways. For example, any of the connections 370 and 380 may be varied. Any of the connections 370 and 380 may be a hard-wired connection. A hard-wired connection may involve connecting the devices through a USB (universal serial bus) port, serial port, parallel port, or other type of wired connection that can facilitate the transfer of data and information between a processor of a device and a second processor of a second device. In another embodiment, any of the connections 370 and 380 may be a dock where one device may plug into another device. In other embodiments, any of the connections 370 and 380 may be a wireless connection. These connections may take the form of any sort of wireless connection, including, but not limited to. Bluetooth connectivity, Wi-Fi connectivity, infrared, visible light, radio frequency (RF) signals, or other wireless protocols/methods. For example, other possible modes of wireless communication may include near-field communications, such as passive radio-frequency identification (RFID) and active RFID technologies. RFID and similar near-field communications may allow the various devices to communicate in short range when they are placed proximate to one another. In yet another embodiment, the various devices may connect through an internet (or other network) connection. That is, any of the connections 370 and 380 may represent several different computing devices and network components that allow the various devices to communicate through the internet, either through a hard-wired or wireless connection. Any of the connections 370 and 380 may also be a combination of several modes of connection.

The configuration of the devices in FIG. 2 is merely one physical system on which the disclosed embodiments may be executed. Other configurations of the devices shown may exist to practice the disclosed embodiments. Further, configurations of additional or fewer devices than the ones shown in FIG. 2 may exist to practice the disclosed embodiments. Additionally, the devices shown in FIG. 2 may be combined to allow for fewer devices than shown or separated such that more than the three devices exist in a system. It will be appreciated that many various combinations of computing devices may execute the methods and systems disclosed herein. Examples of such computing devices may include other types of medical devices and sensors, infrared cameras/detectors, night vision cameras/detectors, other types of cameras, radio frequency transmitters/receivers, smart phones, personal computers, servers, laptop computers, tablets, blackberries, RFID enabled devices, or any combinations of such devices.

Figure 3:
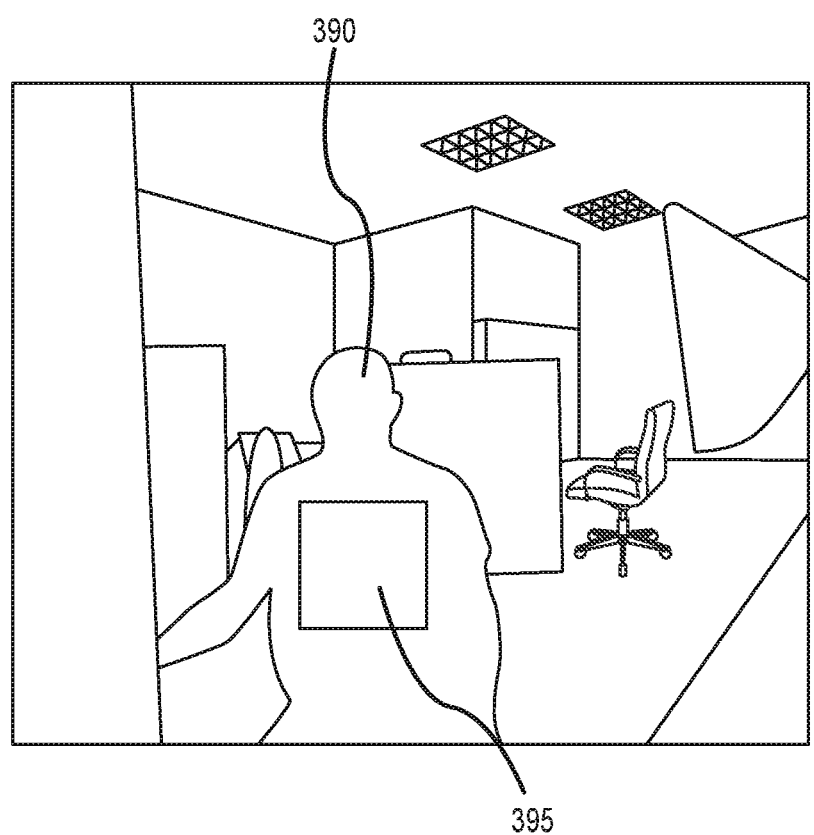
FIG. 3 is an image captured by a camera according to various embodiments described herein.

FIG. 3 is an image captured by a camera according to various embodiments described herein. In this particular example, the image in FIG. 3 is a depth image or depth map captured by a depth sensing camera, such as a Kinect camera from Microsoft. The depth image includes information about the distance from the camera to each point in the image. This type of image or map can be obtained by a stereo camera, a camera cluster, camera array, or a motion sensor. When multiple depth images are taken over time in a video stream, the video information includes the movement of the points within the image, as they move toward and away from the camera over time.

Figure 4:
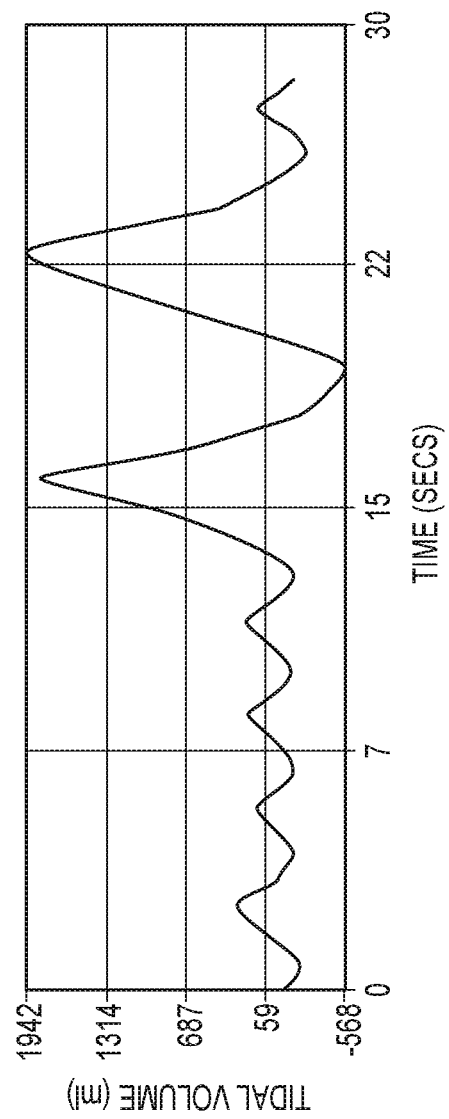
FIG. 4 is a graph showing a tidal volume calculation over time according to various embodiments described herein.
Figure 5:
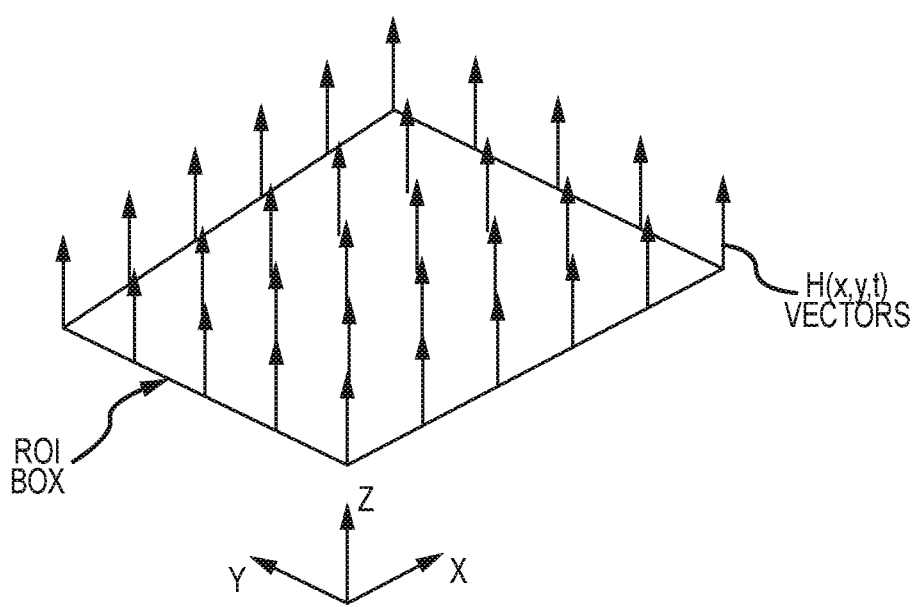
FIG. 5 is a diagram showing how tidal volume associated with a region of interest (ROI) may be calculated according to various embodiments described herein.

The image includes a patient 390 and a region of interest (ROI) 395. The ROI 395 can be used to determine a volume measurement from the chest of the patient 390. The ROI 395 is located on the patient's chest. In this example, the ROI 395 is a square box. In various embodiments, other ROIs may be different shapes. Because the image includes depth data, such as from a depth sensing camera, information on the spatial location of the patient 390, and therefore the patient's chest and the ROI 395, can also be determined. This information can be contained within a matrix, for example. As the patient 390 breathes, the patient's chest moves toward and away from the camera, changing the depth information associated with the images over time. As a result, the location information associated with the ROI 395 changes over time. The position of individual points within the ROI 395 may be integrated across the area of the ROI 395 to provide a change in volume over time as shown in FIGS. 4 and 5. FIG. 4 is a graph showing a tidal volume calculation over time according to various embodiments described herein.

FIG. 5 is a diagram showing how tidal volume associated with a region of interest (ROI) may be calculated according to various embodiments described herein. Vectors associated with points within the ROI 395 are depicted in FIG. 5, where a schematic of the box values are shown to change over time. For example, these vectors represent movement of a patient's chest toward a camera as the patient's chest expands forward with inhalation. Similarly, the vectors will then move backward, away from the camera, when the patient's chest contrasts with exhalation. This movement forward and backward can be tracked to determine a respiration rate. Furthermore, this movement forward and backward can be integrated to determine a tidal volume, as shown in FIG. 5. By integrating the perpendicular vector values H(x,y,t) across the x and y coordinates of the box, the instantaneous volume may be generated as follows in Equation 1:

$$V(t) = \iint H(x,y,t)\,dx\,dy \quad [1]$$

The initial values of H may be set to zero when the analysis of the box is first activated. Therefore, a volume signal V(t) such as the one shown in FIG. 4 may be generated. The volume signal in FIG. 4 shows four shallow breaths followed by two deep breaths then another shallow breath undertaken by the patient 390. The peaks and valleys of the signal in FIG. 4 can be used to identify individual breaths, the size of individual breaths, and a patient's overall respiration rate. Further methods as disclosed herein can be utilized to calibrate these measurements to produce a true tidal volume of the patient 390.

Figure 6:
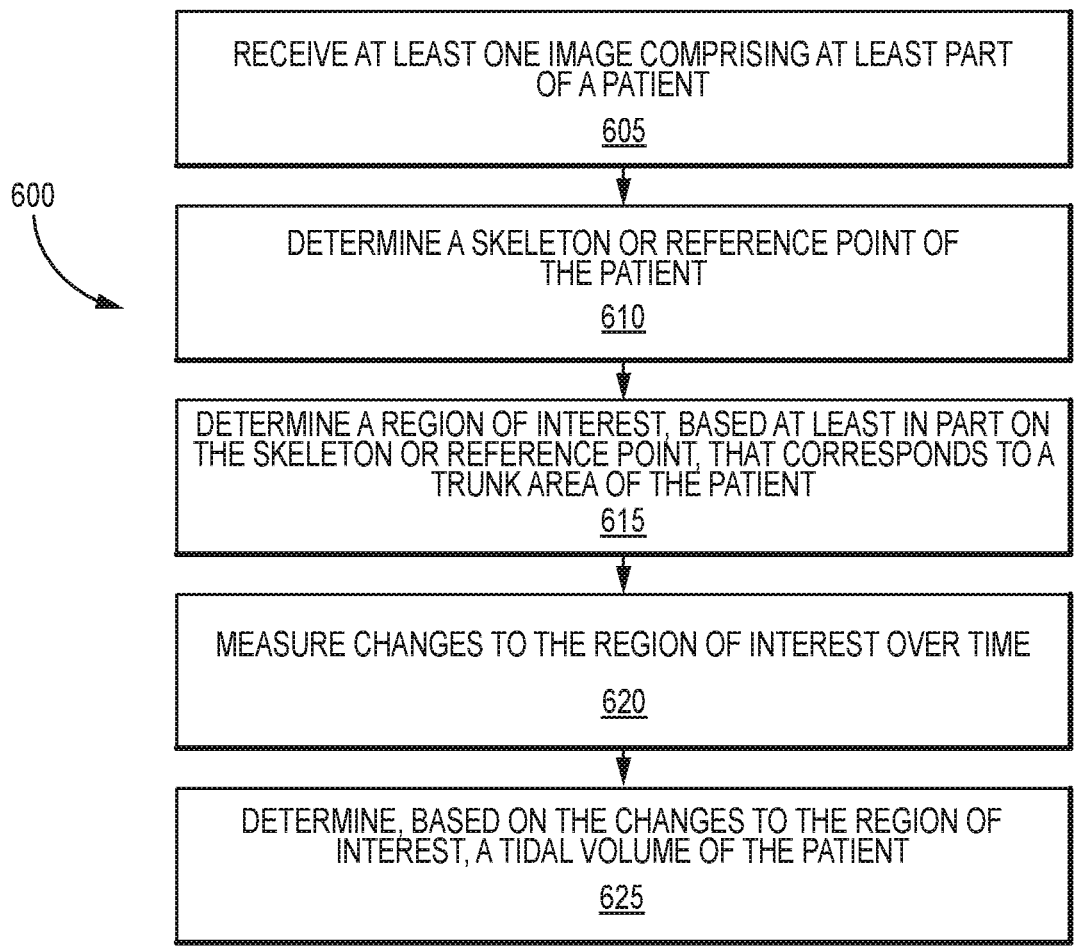
FIG. 6 is a flowchart of a method for determining a region of interest (ROI) and measuring tidal volume according to various embodiments described herein.

FIG. 6 is a flowchart of a method 600 for determining a region of interest (ROI) and measuring tidal volume according to various embodiments described herein. The method 600 includes receiving at least one image comprising at least part of a patient at 605. The method 600 further includes determining a skeleton or reference point of the patient at 610. The method 600 further includes determining a region of interest (ROI) based at least in part on the skeleton or reference point at 615. In some embodiments, methods or measurements other than a skeleton may be used to determine the ROI. For example, the system may identify points on the patient's body (such as shoulders, head, neck, waist, etc.) that correspond to specific places that can be used as a centroid, reference, or flood fill point for forming an ROI. The system may also use information from a depth sensing camera to determine other information about a patient. For example, the system may determine how far away from the camera a patient is using a depth sensing camera or other depth sensing technology. Once that information is known, the system can use the ROI and/or other points of the body that are determined to calculate approximate size of a body or parts of the body. For example, the system may map determined ROI dimensions or other determined information about a patient to approximate size, height, weight, BMI, age, sex, or another characteristic of a patient.

The method 600 further includes measuring changes to the ROI over time at 620. This may be accomplished in various ways as disclosed herein. The method 600 further includes determining, based on the changes to the region of interest, a tidal volume of the patient at 625. This determination can be performed in using any of the methods, systems, and computer readable media disclosed herein.

In some embodiments, the volume signal from the non-contact system may need to be calibrated to provide an absolute measure of volume. For example, the volume signal obtained from integrating points in a ROI over time may accurately track a patient's tidal volume and may be adjusted by a calibration factor. The calibration or correction factor could be a linear relationship such as a linear slope and intercept, a coefficient, or other relationships. As an example, the volume signal obtained from a video camera may under-estimate the total tidal volume of a patient, due to underestimating the volume of breath that expands a patient's chest backward, away from the camera, or upward orthogonal to the line of sight of the camera. Thus, the non-contact volume signal may be adjusted by simply adding or applying a correction or calibration factor. This correction factor can be determined in a few different ways. In one embodiment, an initial reference measurement is taken with a separate flow measurement device. For example, the tidal volume of the patient may be measured using a flow measurement device (e.g. a spirometer) to produce a reference tidal volume over a short calibration or test time frame (such as 3 to 4 breaths). The V(t) signal (also referred to herein as the volume signal, the tidal volume, and/or the tidal volume signal) over the same time frame is compared to the reference tidal volume, and a calibration factor is determined so that the range of V(t) matches the reference tidal volume measured by the flow measurement device. After a few calibration breaths through the flow measurement device, it may be removed from the patient. The V(t) volume signal measured thereafter from the video feed is adjusted using the calibration factor determined during the initial calibration phase.

Figure 7B:
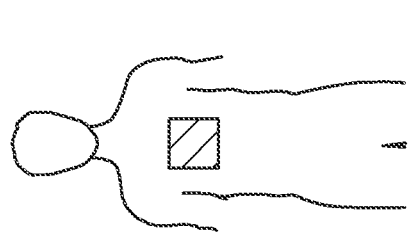
FIGS. 7A-7D are diagrams showing examples of different ROIs for different sized patients according to various embodiments described herein.

In some embodiments, demographic data about a patient may be used to calibrate the volume signal. From a knowledge of the patient's demographic data, which may include height, weight, chest circumference, BMI, age, sex, etc., a mapping from the measured V(t) to an actual tidal volume signal may be determined. For example, patients of smaller height and/or weight may have less of a weighting coefficient for adjusting measured V(t) for a given ROI box size than patients of greater height and/or weight. Different corrections or mappings may also be used for other factors, such as whether the patient is under bedding, type/style of clothing worn by a patient (e.g., t-shirt, sweatshirt, hospital gown, dress, v-neck shirt/dress, etc.), thickness/material of clothing/bedding, a posture of the patient, and/or an activity of the patient (e.g., eating, talking, sleeping, awake, moving, walking, running, etc.). FIGS. 7A-7D are diagrams showing examples of different ROIs for different sized patients according to various embodiments described herein. In other words, even though the ROI boxes of each of the patients in FIGS. 7A and 7B are the same size, the measured V(t) can be adjusted according to the actual size of the patient so that the reported V(t) is more accurate. Thus, if the true tidal volume ($V_{True}$) is related to the video measured tidal volume from the ROI ($V_{ROI}$) as follows in Equation 2:

$$V_{True} = K \cdot V_{ROI} + C \quad [2]$$

where K and C are constants, then K and/or C may be varied according to demographic information. Note that C may be zero or non-zero.

Figure 7D:
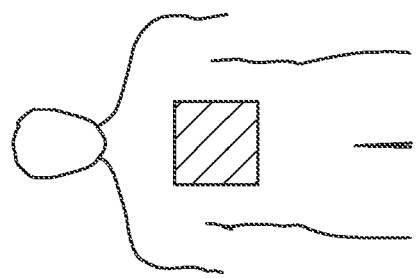
Figure 7A:
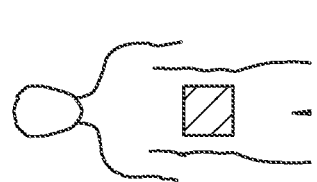
Figure 7C:
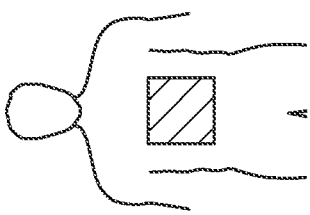

Alternatively, the ROI size may be set according to the patient demographics, i.e., patients of smaller height and/or weight may use a smaller ROI size than patients of greater height and/or weight, such as shown in FIGS. 7C and 7D. Thus, the ROI boxes are scaled according to the patient's size to provide a consistency of the measured part of the body from patient to patient. This scaling can be done based on inputs of a patient's demographics, or may be done based on sensing a different size patient in the image captured by the camera, or by input from a user such as clinician.

The ROI sizes may also differ according to the distance of the patient from the camera system. The ROI dimensions may vary linearly with the distance of the patient from the camera system. This ensures that the ROI scales according with the patient and covers the same part of the patient regardless of the patient's distance from the camera. When the ROI is scaled correctly based on the patient's position in the field of view, the resulting tidal volume calculation from the volume signal V(t) can be maintained, regardless of where the patient is in the field of view. That is, a larger ROI when the patient is closer to the camera, and a smaller ROI when the same patient is further from the camera, should result in the same V(t) calculation. This is accomplished by applying a scaling factor that is dependent on the distance of the patient (and the ROI) from the camera. In order to properly measure the tidal volume of a patient, the actual size of an ROI (the area of the ROI) is determined. Then movements of that ROI (see, e.g., FIG. 5) are measured. The measured movements of the ROI and the actual size of the ROI are then used to calculate a tidal volume. Because a patient's distance from a camera can change, an ROI associated with that patient can appear to change in size in an image from a camera. However, using the depth sensing information captured by a depth sensing camera or other type of depth sensor, the system can determine how far away from the camera the patient (and their ROI) actually is. With this information, the actual size of the ROI can be determined, allowing for accurate measurements of tidal volume regardless of the distance of the camera to the patient.

Figure 8:
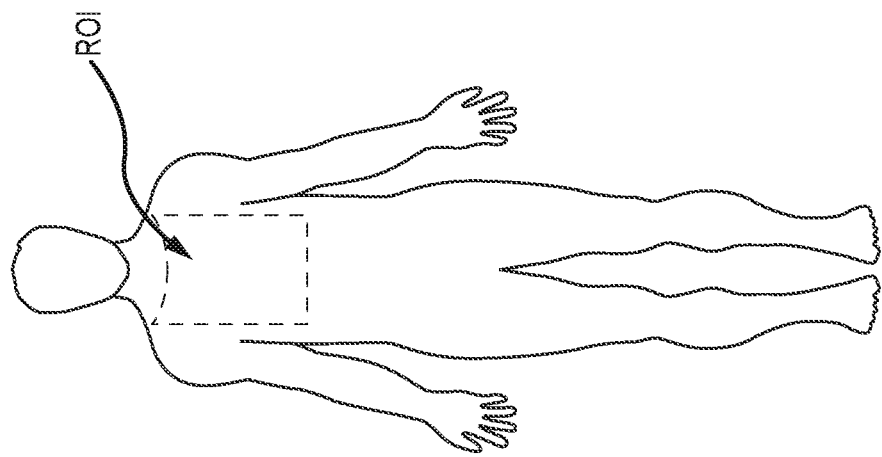
FIG. 8 is a diagram showing a complex ROI according to various embodiments described herein.

Instead of a box of a preset or scaled size, the ROI may instead have a more complex morphology to capture the whole chest region of the patient. An example of this is shown in FIG. 8, which is a diagram showing a complex ROI according to various embodiments described herein. This approach may use a flood field method and/or a method which identifies the outline of the patient to determine the ROI.

Another type of smart ROI determination may use respiration rate (RR) modulations power analysis. This compares a power while breathing to a power while not breathing to filter noise and determine more accurate ROIs and tidal volumes. In a method, a center of the chest is located based on an image of the patient captured by the camera. A small area in the center of the chest is identified where a good respiratory modulation can be extracted. To do so, the chest may be monitored over time to determine a point where that good respiratory modulation is located. The movement of various points on the chest may be compared with a known or expected respiration rate to ensure that a good point is selected. Then, the full frame/field processing can be performed. A quality metric using a power ratio (Prr/Pnot-rr) will yield a heatmap which can be reduced to an ROI by using a dynamic threshold. Points that modulate at the respiration rate and above a threshold amplitude are added to the ROI, and points that do not modulate at that rate or at that amplitude are discarded. This ROI can be updated dynamically, so that the ROI is continually refreshing to capture the portions of the chest that are moving with breaths, or to track the chest as the patient moves across the field of view. Because the distance to the camera of each point on the chest is known, expected dimensions of the ROI may also be inferred. That is, because the general shape of a chest is known, a system may also make sure that portions of an image included in an ROI fit into an expected human chest or trunk shape. The portions singled out as likely to be human/chest trunk may be determined based on the depth information from the image. The system may also include in an ROI points on the chest that fit into a predetermined distance threshold from the camera, as discussed herein (see, e.g., discussion regarding FIGS. 14 and 33-37). This predetermined distance threshold can be set based on known expected human chest/trunk sizes and dimensions. Furthermore, a dynamic threshold for the heatmap produces a complex chest ROI of expected dimension, and shape. In addition, in some embodiments as disclosed herein, an ROI may include more than one non-connected or non-contiguous areas. Those non-connected or non-contiguous areas may also be dynamically determined according to similar methods as a single contiguous/connected ROI.

Where a center point is used to derive an ROI, the center point on the chest may become blocked in some instances, such as when a hand moves in front of the determined center point of the chest. In that instance, the ROI may erroneously track the hand, instead of the chest. In order to counteract this, the system may monitor the center point to ensure that it has good respiratory modulation, i.e. that the center point moves similarly to a human breathing. If that center point (or any other point used) ceases to move with a frequency akin to human respiratory modulation, a new center point may be sought, where human respiratory modulation is occurring. Once such a new point is identified, the region around that point can be filled in to form a new ROI. In some embodiments, that method may be used to find a point around which the ROI should be filled-in in the first instance (rather than attempting to locate a center point of the chest).

In some embodiments, multiple points that show a characteristic similar to respiratory modulations may be selected and used to fill out one or more ROIs on a body. This can advantageously result in identifying any part of the body, not just a chest area, that moves as a result of breathing. Additionally, this method can advantageously provide multiple ROIs that may be monitored together to measure tidal volume or respiration rate, or extrapolated to measure tidal volume as if there were only a single ROI. For example, an arm blocking a camera's view of a chest may extend all the way across the chest. The system can then identify at least two points typical of respiratory modulations, one above the arm on the chest and one below the arm on the chest. Two ROIs can be filled out from those points to extend to cover the chest that is not visible to the camera.

That measured data can then be extrapolated to account for the amount of chest blocked by the arm to get a more accurate tidal volume measurement. The extrapolation may also account for the portion of the chest that is being blocked. This may be helpful because different parts of the chest will move to different degrees than others during a breath. The two ROIs above and below may be utilized to determine which part of the chest is being blocked by the arm. For example, if the top ROI is very small and the bottom ROI is comparatively larger, the system can determine that the arm is blocking a higher portion of the chest closer to the neck. If opposite (large top ROI and small bottom ROI), the system can determine that the portion of the chest being blocked is further down toward the waist. Therefore, the system can account for which part of the chest is being blocked when calculating tidal volume.

In order to extract accurate volume changes from a breathing patient using a depth sensing camera, it is important to correctly select the sampling region, which is then used to aggregate the volume changes. An ROI that encompasses as much of the patient's trunk as possible can advantageously be more accurate than a smaller ROI in capturing complete respiratory motion of a patient. Accordingly, an ROI may be dynamically selected, so that an optimum sampling region based on depth data and skeleton coordinates is continually determined and refreshed as described below.

Figure 9:
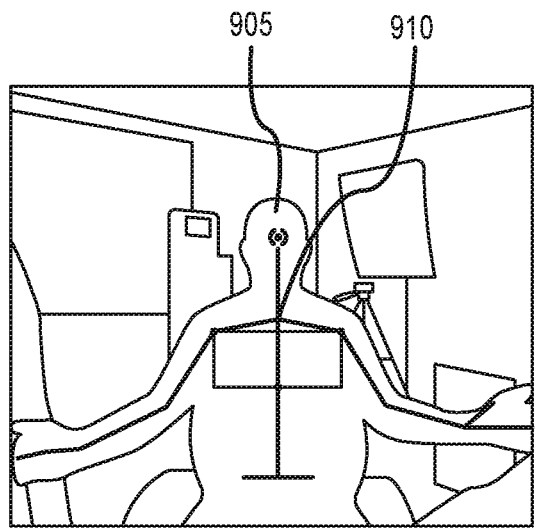
FIG. 9 is a diagram showing a patient with a superimposed skeleton according to various embodiments described herein.

FIG. 9 is a diagram showing a patient 905 with a superimposed skeleton 910 according to various embodiments described herein. Depth data from a depth sensing camera and inferred skeletal information are presented in FIG. 9. Positions from the skeleton data can be used to define a breathing ROI (the rectangle) in which it is safe to expect to find strong respiratory modulation. This breathing ROI is made to extend from both shoulder joints (each indicated by a dot at the top corners of the rectangle), and down to a mid-spine joint (indicated by a dot in the middle of the bottom line of the rectangle). The shading within the image indicates depth information: the darker gray that outlines a body is relatively closer to the camera, while the lighter gray on the walls represents portions of the image that are farther from the camera. The 3D information in an image may be encoded in a way that allows for greater contrast than can be shown in the gray scale images of FIGS. 9-21. For example, the depth information may be shown using RGB data points. In another example, pixels or coordinates of an image may be associated with a depth value that is used to calculate tidal volume according to the systems, methods, and computer readable media disclosed herein.

Figure 10:
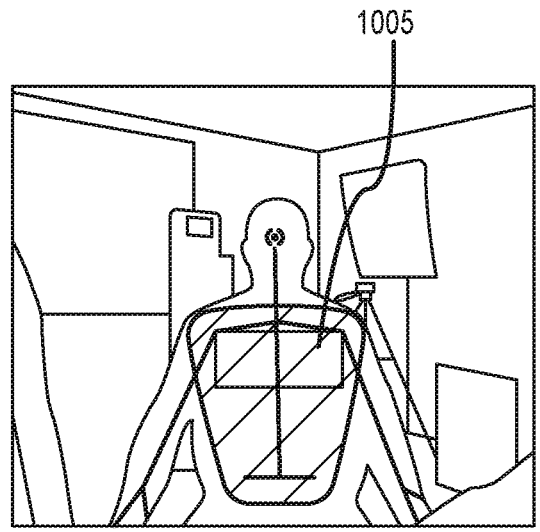
FIG. 10 is a diagram showing a patient with a superimposed skeleton and ROI according to various embodiments described herein.

FIG. 10 is a diagram showing a patient with a superimposed skeleton and ROI according to various embodiments described herein. A two-dimensional body mask 1005 can also be inferred from the skeletal coordinates and encompasses the breathing ROI. The two-dimensional body mask 1005 is defined in FIG. 10 to encompass the patient's trunk by using a dilated pentagon with corners located at: 1) right shoulder, 2) right hip, 3) left hip, 4) left shoulder, and 5) neck joint (at or near cervical vertebrae C7). In various embodiments, other shapes, dilations, or other shape modifications may be used to determine the two-dimensional body mask. In some embodiments, a shape for determining the two-dimensional body mask may be selected based on the shape of the patient's body, demographic data of the patient, an orientation of the patient's body, or any other factor. The mask here is a reasonable approximation of the actual torso boundaries within the 2D depth image (the data in a 2D depth image encodes 3D information so that changes in depth in a 3D space can be detected and utilized to calculate tidal volume as disclosed herein).

Figure 11:
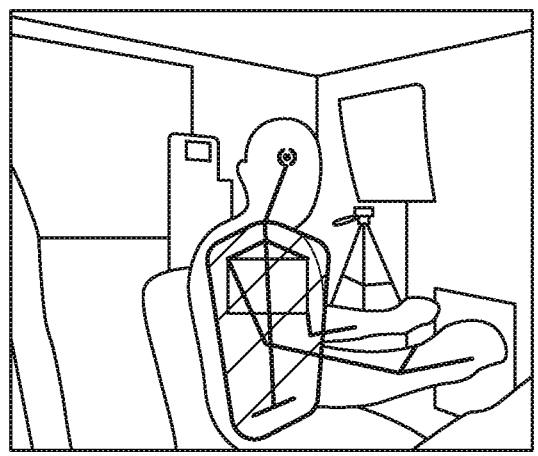
FIG. 11 is a diagram showing a patient with an ROI turned to face a first direction according to various embodiments described herein.
Figure 12:
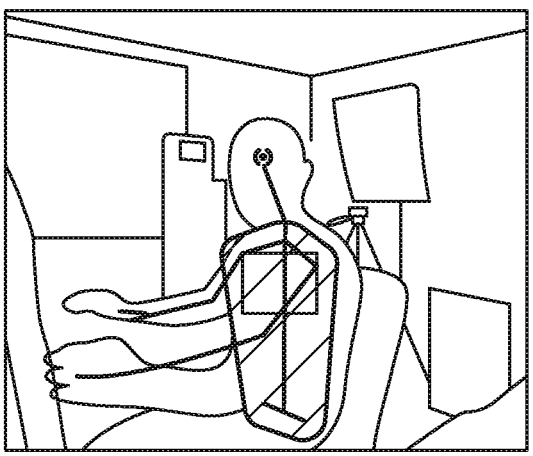
FIG. 12 is a diagram showing a patient with an ROI turned to face a second direction according to various embodiments described herein.

FIG. 11 is a diagram showing a patient with an ROI turned to face a first direction (patient facing toward the right on the page) according to various embodiments described herein. FIG. 12 is a diagram showing a patient with an ROI turned to face a second opposite direction (toward the left on the page) according to various embodiments described herein. As shown in FIGS. 11 and 12, the dynamically-generated mask can follow rotations of the torso relative to the camera.

Figure 13:
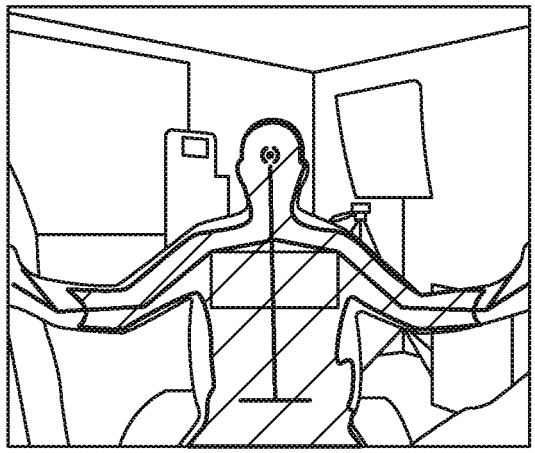
FIG. 13 is a diagram showing a patient with an ROI that has been flood filled according to various embodiments described herein.

FIG. 13 is a diagram showing a patient with an ROI that has been flood filled according to various embodiments described herein. A two-dimensional depth mask can also be created from the depth image using a depth-based flood fill method. In other words, parts of the image that are within a certain depth range from the camera are flood filled to represent the ROI. A seed coordinate is place within the breathing ROI. In this case, the center of the box was used. A depth tolerance range can be defined relative to the seed point's depth from the camera: a low tolerance defines the closest allowed pixel, and a high tolerance defines the furthest allowed pixel to be included in the ROI. A flood fill method is applied starting from the seed to find the largest contiguous region contained with that range. This method can identify the patient's chest, when the chest surface is somewhat planar and lies within the specified depth range from the camera. This method can determine hard boundaries of objects as shown in FIG. 13. However, in this particular instance, regions of the patient's body which are not of as great an interest for a respiratory signal (e.g., head, arms) may also be included if they also fall within the same specified depth range. Such regions can be excluded from the ROI if they do not exhibit respiratory modulations.

Figure 14:
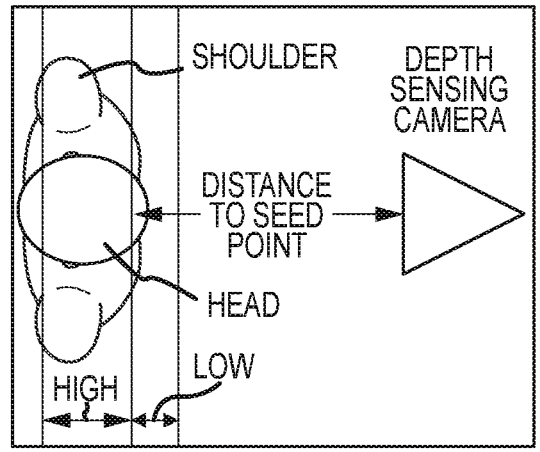
FIG. 14 is a diagram showing an implementation of a depth mask to determine an ROI according to various embodiments described herein.

FIG. 14 is a diagram showing an implementation of a depth mask to determine an ROI according to various embodiments described herein. In particular, FIG. 14 shows how a seed point of the patient exists relative to the depth camera, and how the high and low thresholds for the depth mask may be configured. The "low" threshold sets the distance toward the camera from the seed point, and the "high" threshold sets the distance away from the camera from the seed point. Pixels that fall within these ranges will be included in the ROI. In various embodiments, different thresholds for the high and low thresholds may be utilized.

Figure 15:
FIG. 15 is a diagram showing a patient with an ROI turned to face a first direction, where the ROI has been flood filled and discards the arms according to various embodiments described herein.
Figure 16:
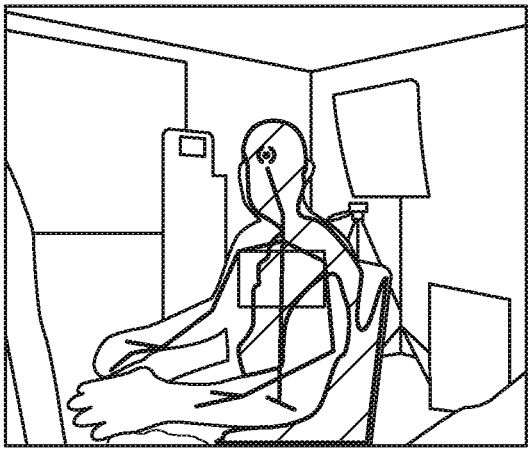
FIG. 16 is a diagram showing a patient with an ROI turned to face a second direction, where the ROI has been flood filled and discards the arms according to various embodiments described herein.

FIG. 15 is a diagram showing a patient with an ROI turned to face a first direction, where the ROI has been flood filled but discards the arms according to various embodiments described herein. FIG. 16 is a diagram showing a patient with an ROI turned to face a second direction, where the ROI has been flood filled but discards the arms according to various embodiments described herein. The flood field is able to handle rotation of the patient because as the patient turns, the patient's arms move too close or far from the camera, and thus move out of the thresholds of the depth mask. Accordingly, the dynamically generated flood field ROI is able to discard obstruction caused by the arms based on the depth range defined. In particular, in both FIGS. 15 and 16, the chest remains within the ROI while the arms are excluded.

Figure 17:
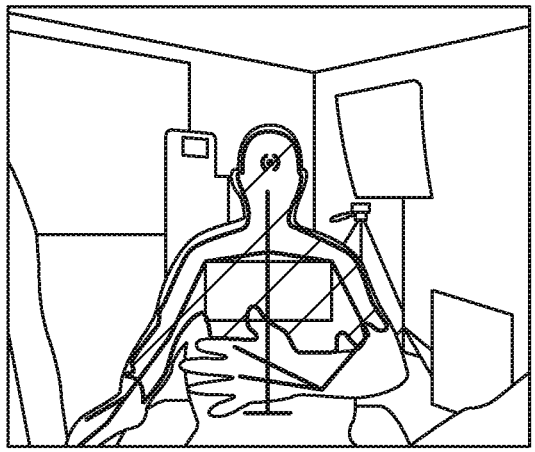
FIG. 17 is a diagram showing a patient with an ROI that does not include the patient's hand according to various embodiments described herein.

FIG. 17 is a diagram showing a patient with an ROI that does not include the patient's hand according to various embodiments described herein. FIG. 17 shows another example of the flood field ability to discard obstruction based on depth values (i.e., using a depth mask). The patient's hand is correctly discarded from the generated ROI because it is too close to the camera.

Figure 18:
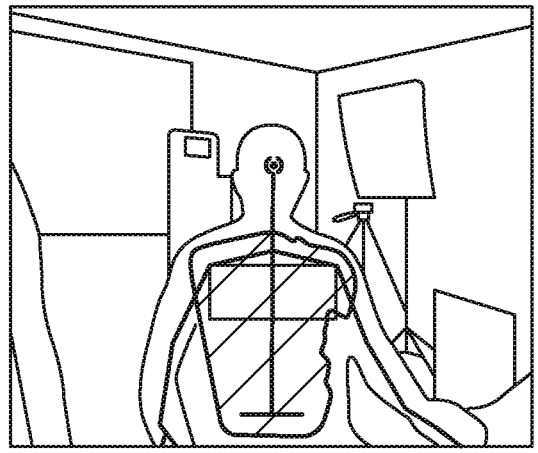
FIG. 18 is a diagram showing a patient with an ROI where the arms and head have been excluded according to various embodiments described herein.

FIG. 18 is a diagram showing a patient with an ROI where the arms and head have been excluded according to various embodiments described herein. In particular, the ROI in FIG. 18 uses a combination of the body mask described above with respect to FIGS. 9-12 and the depth mask described above with respect to FIGS. 13-17 in order to generate an improved sampling region (ROI) from which to extract respiration volumes. In other words, both the methods are applied to an image captured by a camera to get a more accurate ROI, leading to more precise and/or accurate tidal volume measurements. FIG. 18 shows an example ROI where the patient is facing the camera (generally orthogonal to the camera's line of sight), that is generated/determined using both methods combined.

Figure 19:
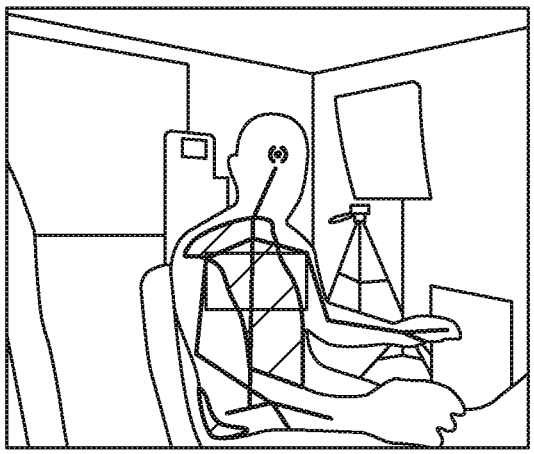
FIG. 19 is a diagram showing a patient with an ROI where the arms and head have been excluded and the patient is turned to face a first direction according to various embodiments described herein.
Figure 20:
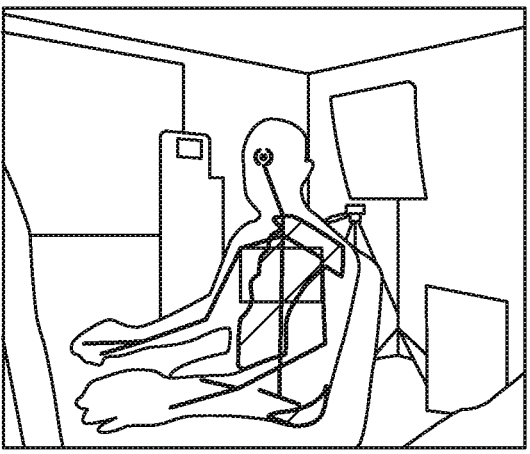
FIG. 20 is a diagram showing a patient with an ROI where the arms and head have been excluded and the patient is turned to face a second direction according to various embodiments described herein.
Figure 21:
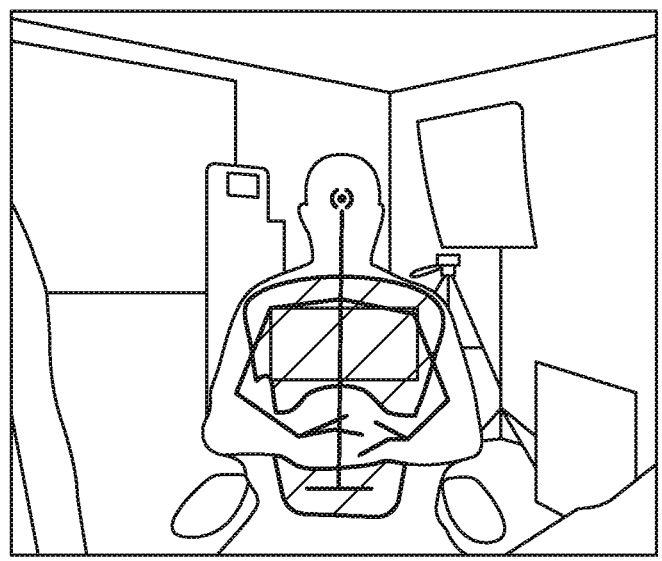
FIG. 21 is a diagram showing a patient with an ROI that does not include the patient's hands according to various embodiments described herein.

FIG. 19 is a diagram showing a patient with an ROI where the arms and head have been excluded and the patient is turned to face a first direction according to various embodiments described herein. FIG. 20 is a diagram showing a patient with an ROI where the arms and head have been excluded and the patient is turned to face a second direction according to various embodiments described herein. When the patient is rotated as in FIG. 19 or FIG. 20, the mask created with the combined method performs better than either of the methods in isolation. There is no overflow of the region that could occur with the flood fill, so the head, arms, chair, etc. are correctly discarded. However, the flood fill method's robustness to boundary obstructions is preserved. FIG. 21 is a diagram showing a patient with an ROI that does not include the patient's hands according to various embodiments described herein. Accordingly, as disclosed herein, various features—the hands, face, etc.—may be identified in the image and filtered out of the ROI on that basis. In some embodiments where obstructions are present, the visible, unobstructed ROI area may be measured and matched to an ideal area (if the whole ROI was visible), and the measured area (visible, unobstructed area) divided by this value (the ideal ROI area) to give an equivalent proportional area for use in a total tidal volume estimation.

Figure 22:
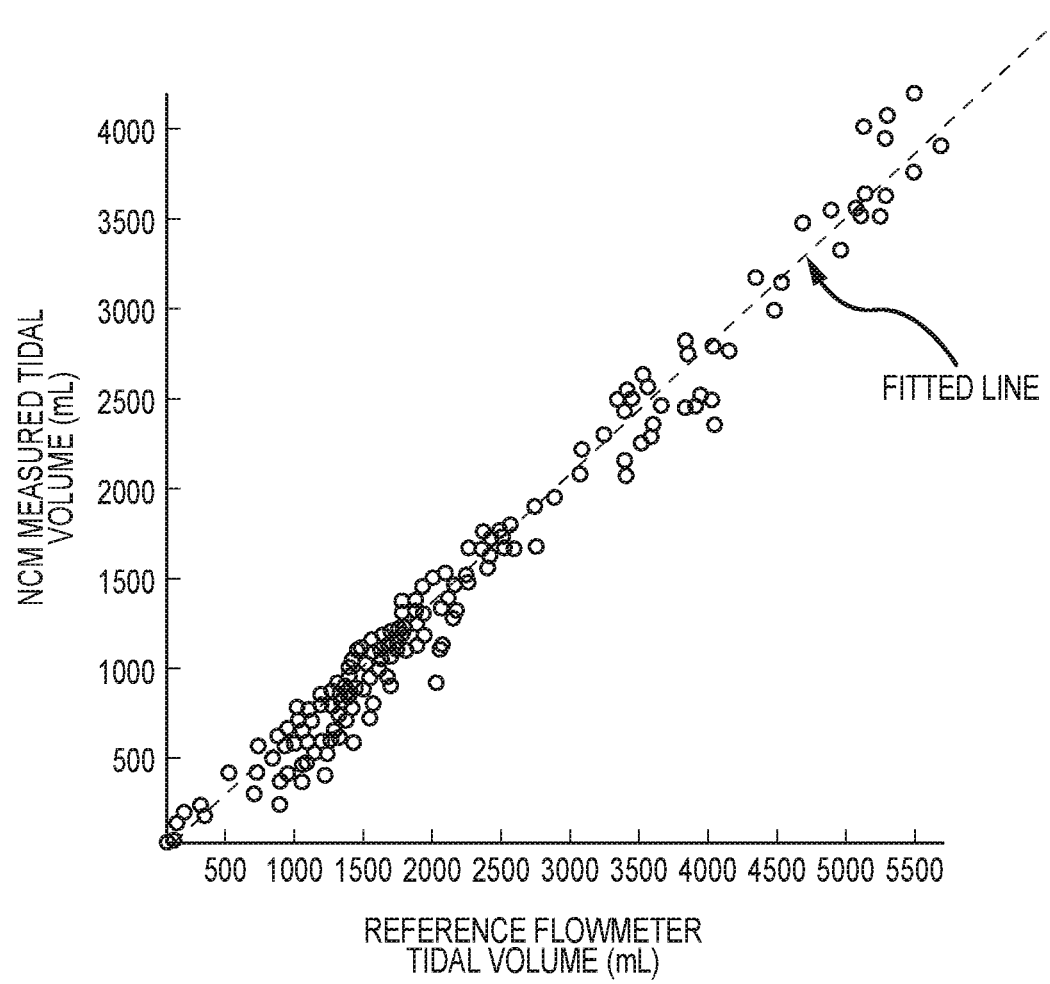
FIG. 22 is a graph showing tidal volume measured by an air flow measurement device as compared to tidal volume measured by non-contact video monitoring according to various embodiments described herein.

With respect to FIGS. 22-25 described below, a true tidal volume may be determined by adjusting a measured non-contact or video tidal volume according to historically collected data which shows a relationship between the non-contact monitoring tidal volume and the reference (the historically collected data). FIG. 22 is a graph showing tidal volume measured by a reference air flow measurement device (x-axis) as compared to tidal volume measured by non-contact video monitoring (y-axis) according to various embodiments described herein. In FIG. 22, over 100 breath volumes determined by a camera system are plotted against volumes determined from a reference air flow meter device.

The figure shows a very clear linear relationship between the two data sets, with a non-identity slope (a slope that is not equal to 1). Thus, a video tidal volume measured from a non-contact video system can easily be translated into an expected true tidal volume by multiplying by a coefficient based on the slope.

A line is fitted to the data. This line may be in the form of a linear regression line with the form of Equation 3 below:

$$TV_m = m \times TV_r + c \qquad [3]$$

where $TV_m$ is the measured tidal volume using the non-contact camera system, $TV_r$ is the reference tidal (true) volume, m is the gradient and c is a constant. In such a method, a regression may be used where the line is forced through the origin of the graph in FIG. 22. This yields Equation 4 below (i.e., c=0):

$$TV_m = m \times TV_r \qquad [4]$$

and the gradient m becomes a simple multiplier constant. Alternatively, a more complex, non-linear equation may be fitted to the data. Alternatively, a piecewise function may also be fitted, or any other relationship. In various embodiments, a series of relationships depending on other factors may be utilized. For example, different curves or fits may be utilized for various respiratory rates, various patient postures, modes of breathing (chest or abdominal), patient demographics (BMI, age, sex, height, weight, etc.), or any other factor.

Figure 23:
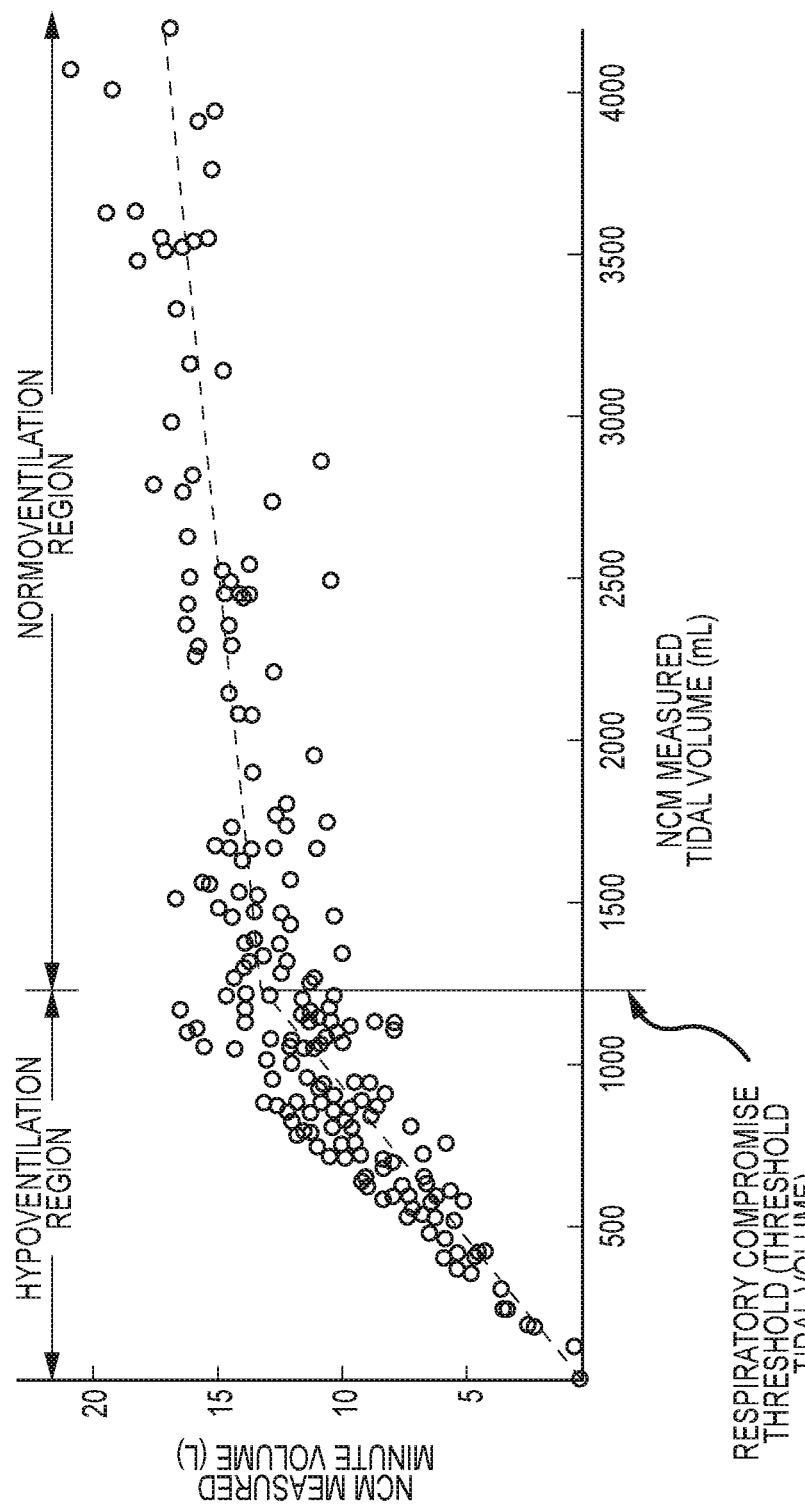
FIG. 23 is a graph showing tidal volume measurements and a respiratory compromise threshold according to various embodiments described herein.

The tidal volume measurement ($TV_m$) may also be used to determine whether a patient is exhibiting hypoventilation. FIG. 23 is a graph showing tidal volume measurements and a respiratory compromise threshold according to various embodiments described herein. In FIG. 23, a plot of $TV_m$ against the measured minute volume ($MV_m$) is shown. Minute volume is the amount of air breathed by a patient per minute. This information is valuable because patients may breathe at different rates and depths (some may breathe longer and deeper, while others breathe shallower but more often). However, the minute volume indicates how much total air is actually being taken in by a patient over time, which can be valuable to indicate whether a patient is in a normal state (e.g., normoventilation) or abnormal state (e.g., hypoventilation, hyperventilation). A distinct kink in the data at the respiratory compromise threshold indicates a lower threshold of normoventilation, below which hypoventilation may be taking place. Above this point the minute volume is relatively constant with increasing tidal volume, increasing only slightly. This relatively constant region indicates that even at larger tidal volumes, minute volume is relatively stable, likely because larger breaths (with larger tidal volume) are taken at lower respiratory rates (breaths per minute), leading to a similar total minute volume. Such a plot may indicate to a clinician that the patient is exhibiting hypoventilation and that an intervention is necessary.

Figure 24:
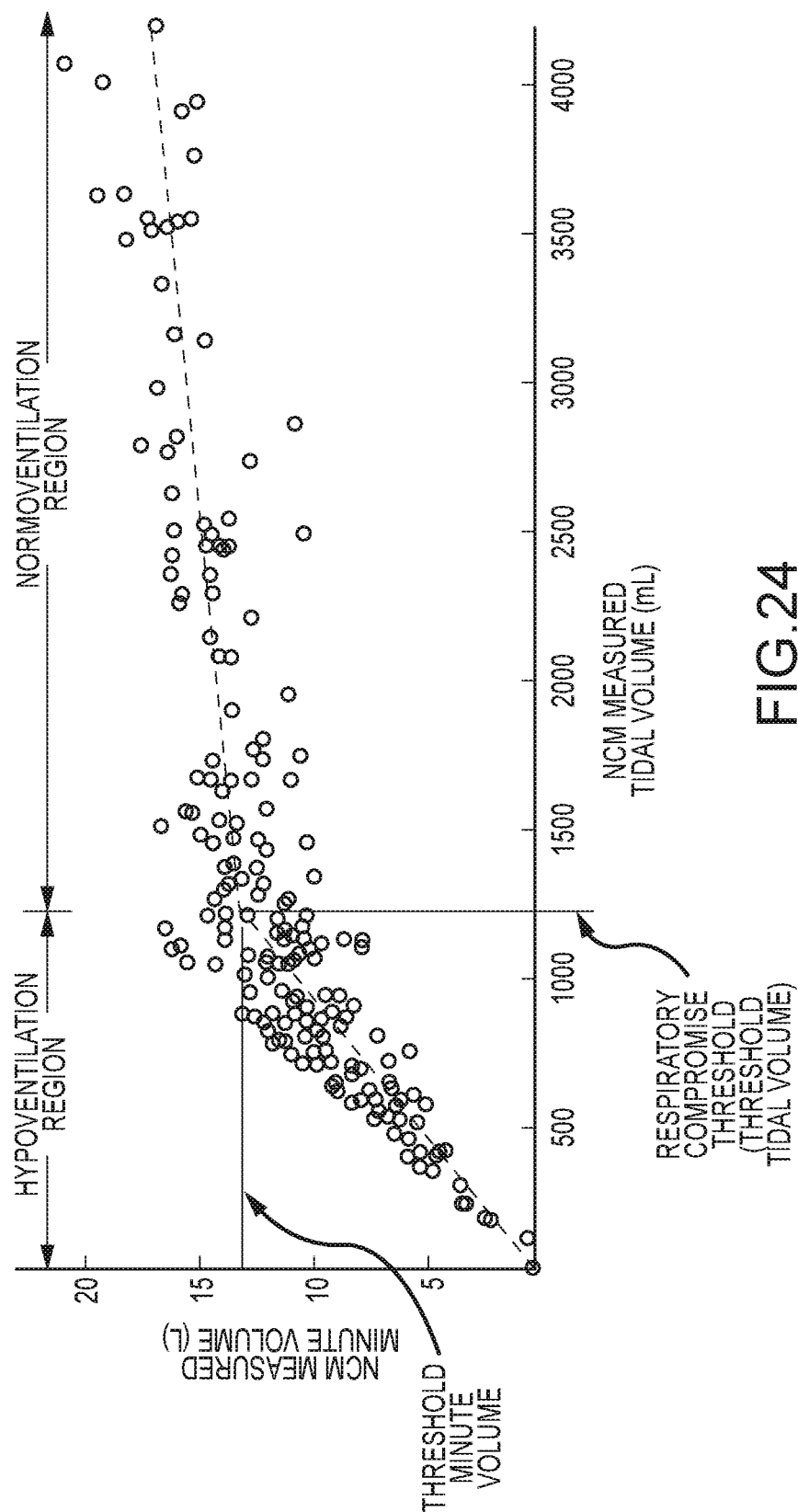
FIG. 24 is a graph showing tidal volume measurements and a threshold tidal volume indicating hypoventilation according to various embodiments described herein.

A threshold minute volume may also be determined as shown in FIG. 24. FIG. 24 is a graph showing tidal volume measurements and a threshold minute volume on the y-axis, indicating hypoventilation according to various embodiments described herein. In other words, a threshold minute volume may be determined that indicates a patient may be in the hypoventilation region. In some embodiments, a moving average may be used since some of the data points in the normoventilation region fall below the threshold minute volume. Hypoventilation can be determined to be present when a patient's tidal volume falls below the x-axis respiratory compromise threshold (e.g., a threshold tidal volume), or the minute volume falls below the y-axis threshold minute volume, or a combination of both, for a minimum duration of time. When hypoventilation is determined, the system may generate an alarm to indicate to healthcare professionals that the patient should be monitored and/or treated.

Figure 25:
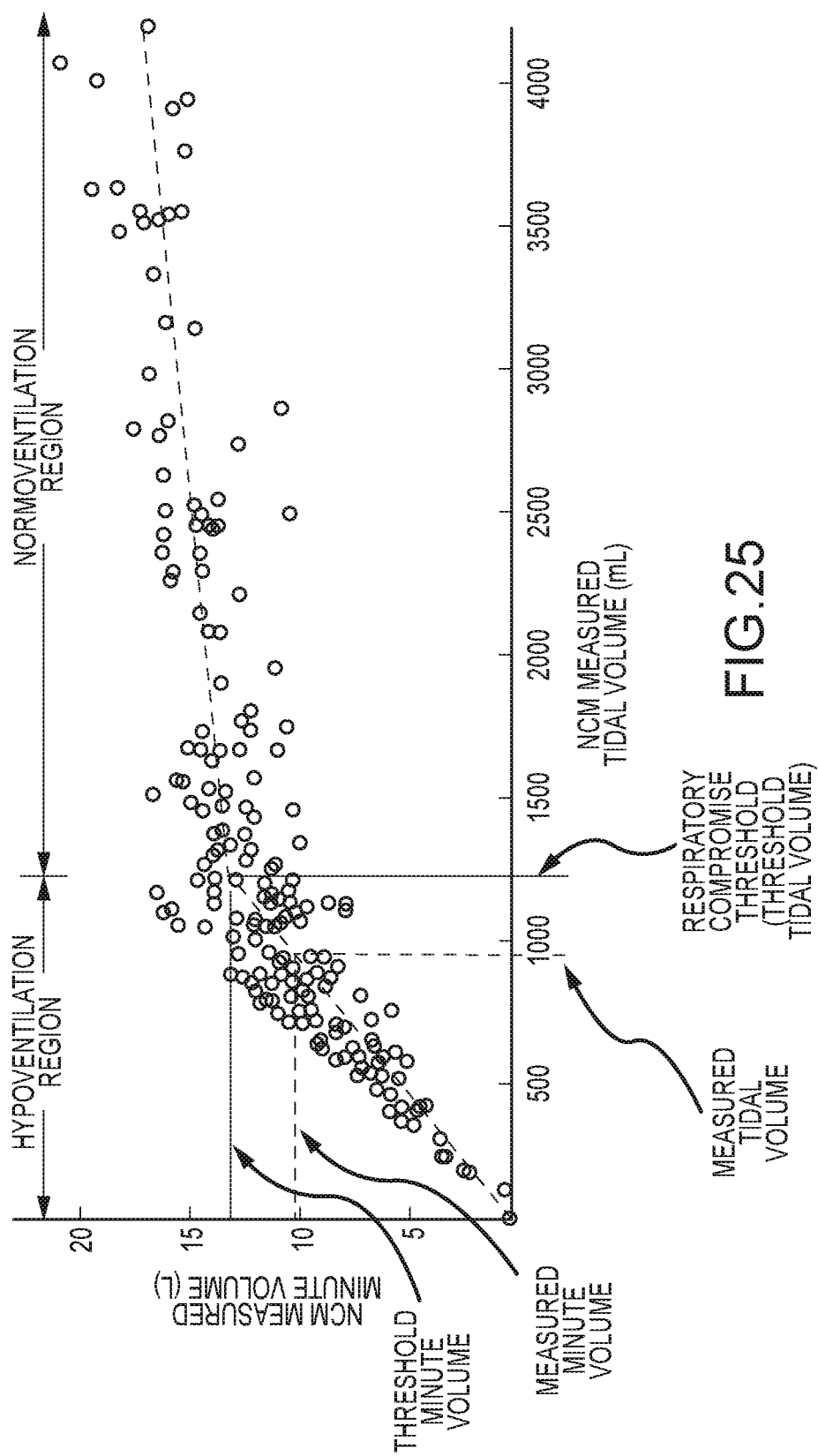
FIG. 25 is a graph showing a measured minute volume that can be used to calculate a degree of compromise according to various embodiments described herein.

FIG. 25 is a graph showing a measured minute volume that can be used to calculate a degree of compromise according to various embodiments described herein. Once below the threshold(s), a degree of compromise may be represented by a ratio of areas as shown on the plot in FIG. 25. That is, the area indicated by the dotted lines can be divided by the area indicated by the solid lines to give an indication of the severity of the respiratory compromise. The dotted lines show where the patient's measurements currently are, and the solid lines indicate the threshold for normal respiration. This ratio can be determined by dividing the measured minute volume by the threshold volume level as shown in FIGS. 24 and 25 and as follows in Equation 5:

$$CD = MV/MV_{threshold} \qquad [5]$$

or alternatively using the measured tidal volume and the respiratory compromise threshold (e.g., the threshold tidal volume) as shown below in Equation 6:

$$CD = TV/TV_{threshold} \qquad [6]$$

It can be seen that these ratios are the same when a data point falls on the fitted line and the fit is linear and goes through the origin. However, they may differ due to a data spread or if other non-linear forms are used. These graphs may be generated on a patient by patient basis to generate custom lines and thresholds, or curves may be applied to tidal volumes measured through non-contact video monitoring that are most likely to fit a patient as disclosed herein.

As mentioned above, the volume signal V(t) from the video image may need to be calibrated or adjusted to obtain a true tidal volume. For example, the image in FIG. 3 above was captured with the patient sitting with their back pressed against a seat and facing the camera. Accordingly, the plane of the chest of the patient is orthogonal to the camera. Disclosed herein are methods for calculating a tidal volume in instances where the plane of a patient's chest is not orthogonal to a camera's line of sight.

Figure 26:
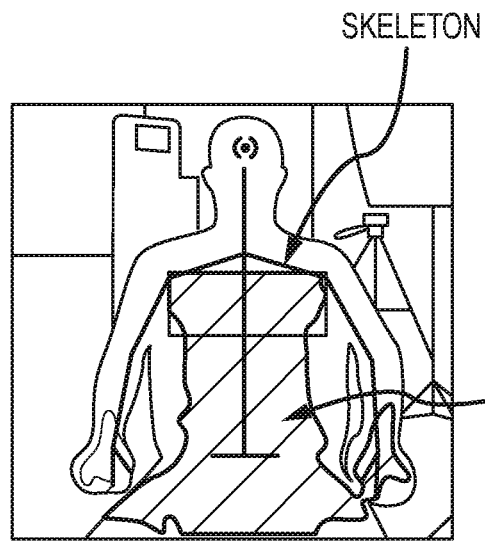
FIG. 26 is a diagram showing an ROI with a flood fill region according to various embodiments described herein.

If the patient is sitting at an angle to the camera, a motion vector associated with respiration of the patient may not be in line with the camera's line of sight. FIG. 26 is a diagram showing an ROI with a flood fill region according to various embodiments described herein. FIG. 26 shows the skeleton superimposed onto the depth image of the patient. Also shown in FIG. 26 is the flood fill region of the ROI. In this embodiment, the ROI is defined within a distance from the center of the chest. Such method works well if the chest is orthogonal to the line of sight of the camera.

Figure 27:
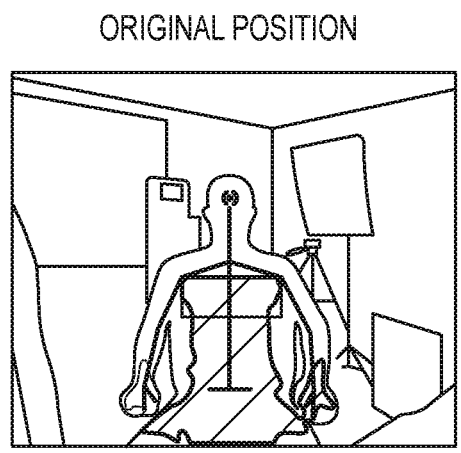
FIG. 27 is a diagram showing a patient at an original position according to various embodiments described herein.
Figure 28:
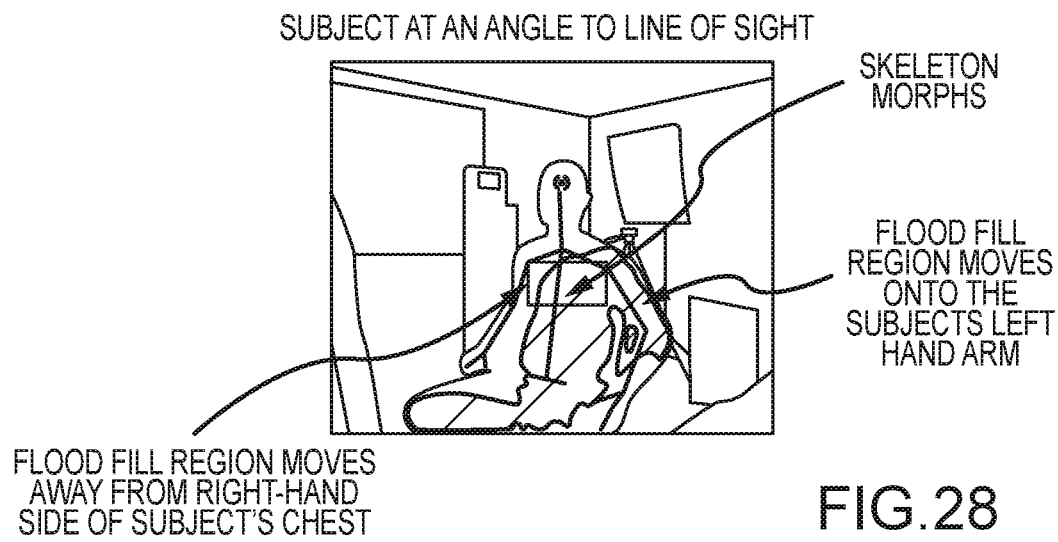
FIG. 28 is a diagram showing a patient at an angle to a line of sight of a camera according to various embodiments described herein.

FIG. 27 is a diagram showing a patient at an original position according to various embodiments described herein. FIG. 28 is a diagram showing a patient at an angle to a line of sight of a camera according to various embodiments described herein. In other words, FIG. 28 shows the flood fill region on the patient once he/she has rotated to sit at an angle to the camera's line of sight. Comparing this region with the original in FIG. 27, the flood fill region has moved onto the side of the patient covering part of the left arm and moving away from the right-hand part of the chest.

Figure 30:
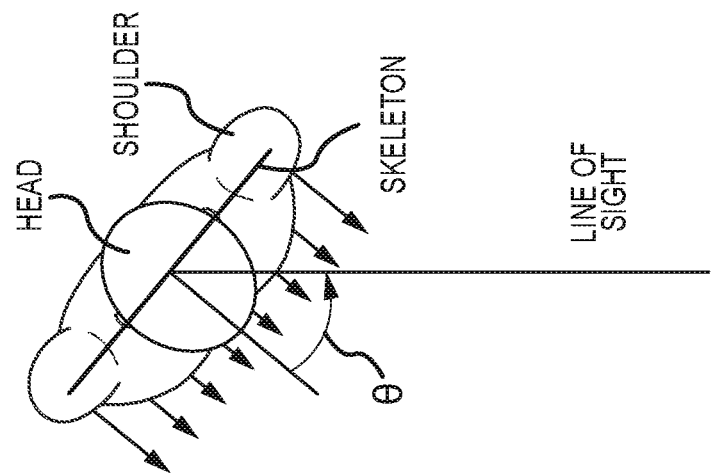
FIG. 30 is a diagram showing a representation of a patient at an angle to a line of sight of a camera from above according to various embodiments described herein.
Figure 29:
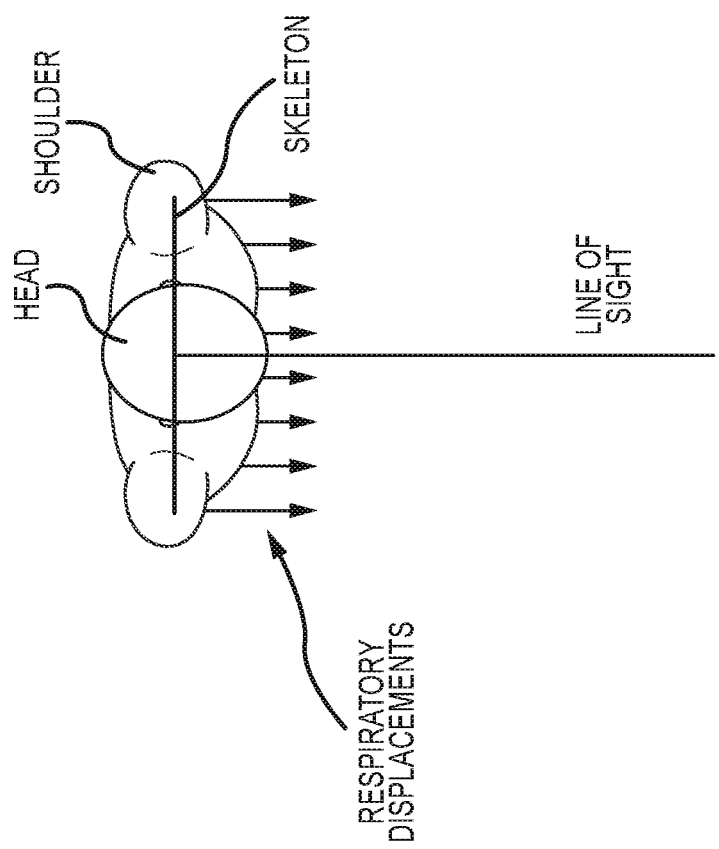
FIG. 29 is a diagram showing a representation of a patient from above according to various embodiments described herein.

An improved method is disclosed herein for correcting this movement of the flood fill region caused by a non-orthogonal angle of the plane of the chest to the line of sight of the camera. FIG. 29 is a diagram showing a representation of a patient from above according to various embodiments described herein. FIG. 30 is a diagram showing a representation of a patient at an angle to a line of sight of a camera from above according to various embodiments described herein. FIG. 29 shows the patient with their chest plane orthogonal to the line of sight of the camera. Respiratory displacements of the chest are shown. These respiratory displacements are denoted as $d_{i,j}$, where i and j are the indices along the vertical and horizontal plane of chest. These displacements are integrated across the ROI to provide a tidal volume from the depth camera system. FIG. 30 shows the patient sitting at an angle ($\theta$) to the line of sight. In this case, the displacements along the line of sight of the camera $d^*_{i,j}$ will be less than the actual displacements orthogonal to the chest wall. We may correct these displacements by dividing by the cosine of the angle $\theta$ as follows in Equation 7:

$$d_{i,j} = d^*_{i,j}/\cos(\theta) \quad [7]$$

The true tidal volume in the direction of the line of sight may now be calculated by numerically integrating these values according to Equation 8 below:

$$TVc = \Sigma_i \Sigma_j d_{i,j} \Delta \quad [8]$$

where $\Delta$ is the area of the i-j grid tiles. This type of measurement can also be performed if the patient is reclining; that is, if the rotation of the plane of the chest is along a different axis or plane (e.g. along an x axis rather than a y axis as in FIG. 30). Additionally, this type of measurement can be performed if the rotation of the plane of the patient's chest is along multiple axes. These, however are merely examples, and it will be understood that further enhancements to these formulas can be made to account for a twisting of the patient along the torso from shoulders to hips.

The embodiments described above with respect to FIGS. 29 and 30 assume that the volume change of the ROI is solely in a direction orthogonal to the plane of the chest wall. Additional correction factors may be used to take account of the breathing which expands the torso in lateral directions. These correction factors may be applied irrespective of a position or orientation of the chest to the camera.

Figure 32:
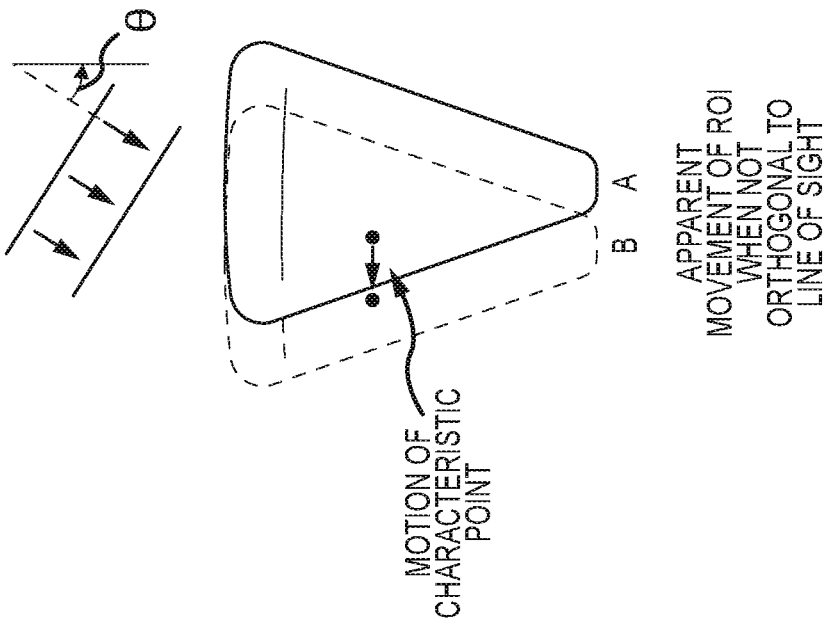
FIG. 32 is a diagram showing apparent movement of an ROI of a patient that is not orthogonal to a line of sight of a camera according to various embodiments described herein.
Figure 31:
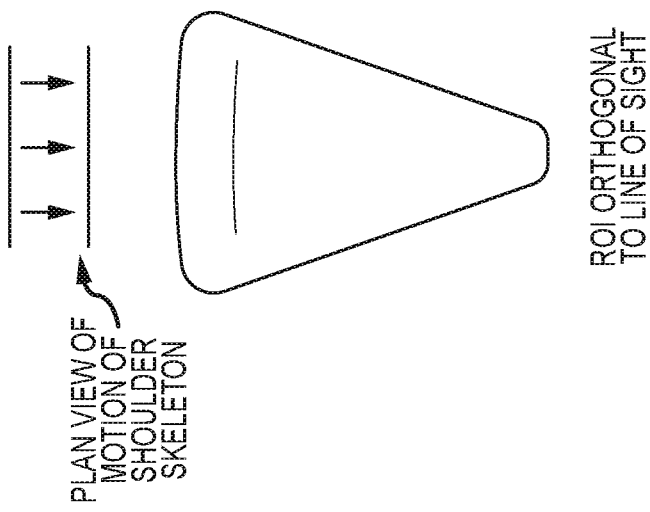
FIG. 31 is a diagram showing apparent movement of an ROI of a patient orthogonal to a line of sight of a camera according to various embodiments described herein.

FIG. 31 is a diagram showing apparent movement of an ROI of a patient orthogonal to a line of sight of a camera according to various embodiments described herein. In other words, the surface of the patient's chest is oriented orthogonal to the line of sight of the camera, and the movement shown is movement, as seen by the camera, of the chest of the orthogonally oriented patient as that patient breathes. FIG. 32 is a diagram showing apparent movement of an ROI of a patient that is not orthogonal to a line of sight of a camera according to various embodiments described herein. In other words, the surface of the patient's chest is oriented non-orthogonally with respect to the camera's line of sight, and the movement shown is movement, as seen by the camera, of the chest of the non-orthogonally oriented patient as that patient breathes. In an embodiment, the lateral motion associated with the chest movement non-orthogonal to the camera line of sight (FIG. 32) can be accounted for. The ROI seen by the camera system in FIG. 32 is compressed in the horizontal direction due to when the patient is non-orthogonal to the line of sight of the camera. As the patient breathes, the apparent position of the ROI will move due to the horizontal component of the chest displacements (this is zero for a perfect orthogonal case (FIG. 31) which has no such movement). Knowing the angle $\theta$, the change in the location of characteristic points on the ROI may be calculated and thus the ROI through the respiratory cycle may be more accurately tracked.

Figure 33:
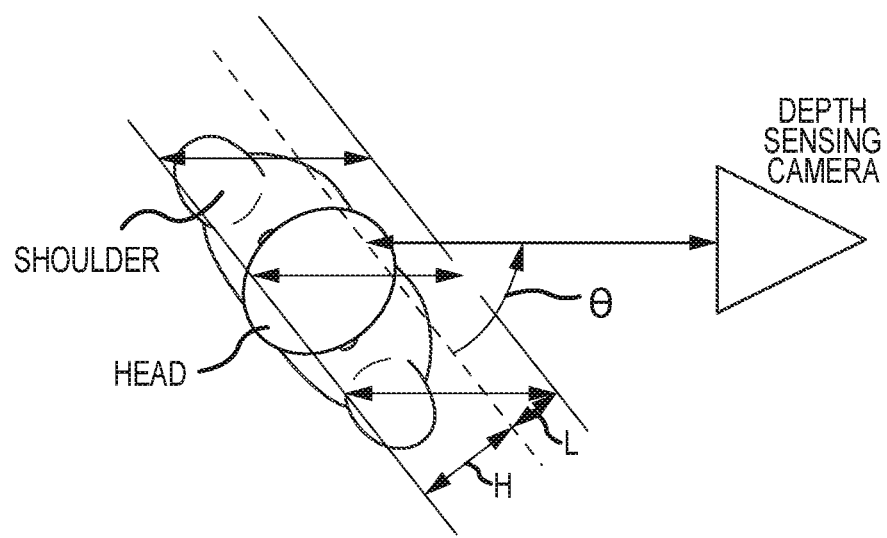
FIG. 33 is a diagram showing an angle at which a patient's ROI is not orthogonal to a line of sight of a camera according to various embodiments described herein.

FIG. 33 is a diagram showing an angle at which a patient's ROI is not orthogonal to a line of sight of a camera according to various embodiments described herein. A transformed flood field box can be defined by knowing the angle $\theta$ as shown in FIG. 33. Surface outside this box may not be included in the flood field. Furthermore, as shown in FIG. 33, the thresholds from a center point on the chest may still be utilized as adjusted according to the angle $\theta$.

Figure 34:
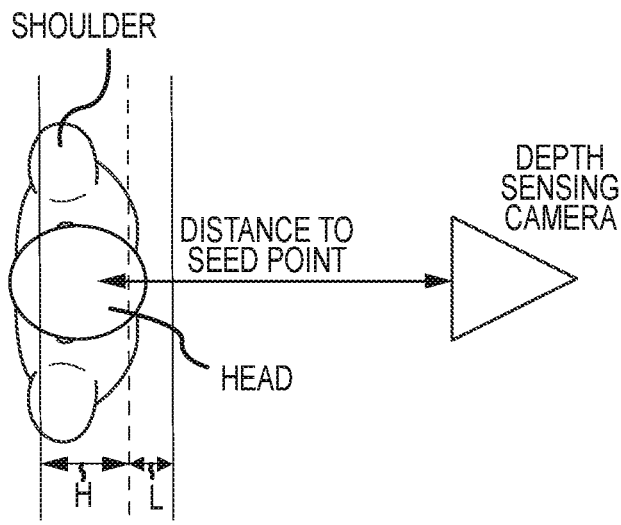
FIG. 34 is a diagram showing a representation of different depth thresholds associated with a patient orthogonal to a line of sight of a camera according to various embodiments described herein.
Figure 35:
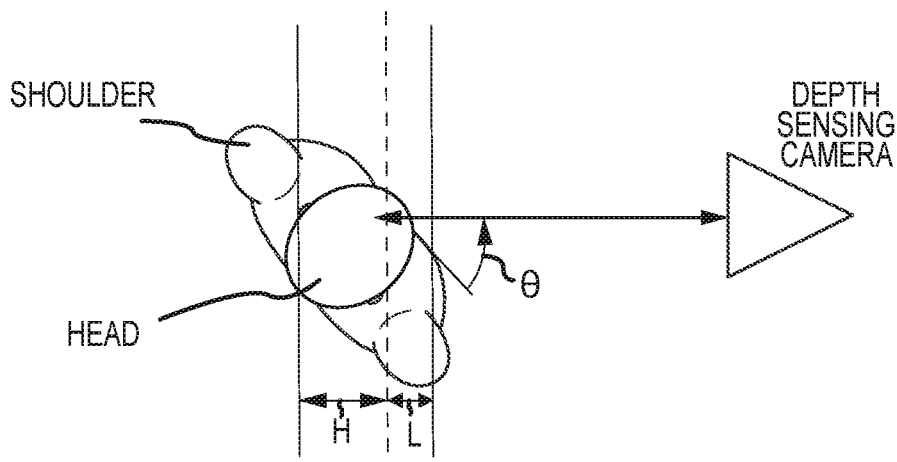
FIG. 35 is a diagram showing a representation of unadjusted depth thresholds with respect to a patient that is not orthogonal to a line of sight of a camera according to various embodiments described herein.
Figure 36:
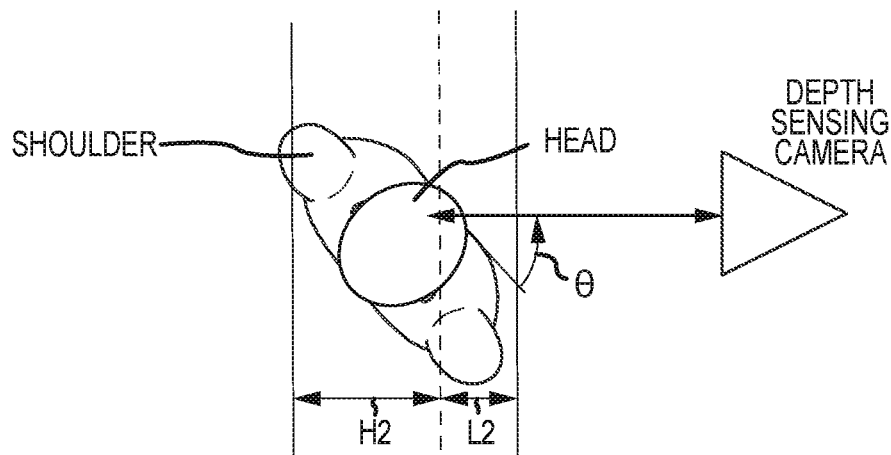
FIG. 36 is a diagram showing a representation of adjusted depth thresholds with respect to a patient that is not orthogonal to a line of sight of a camera according to various embodiments described herein.
Figure 37:
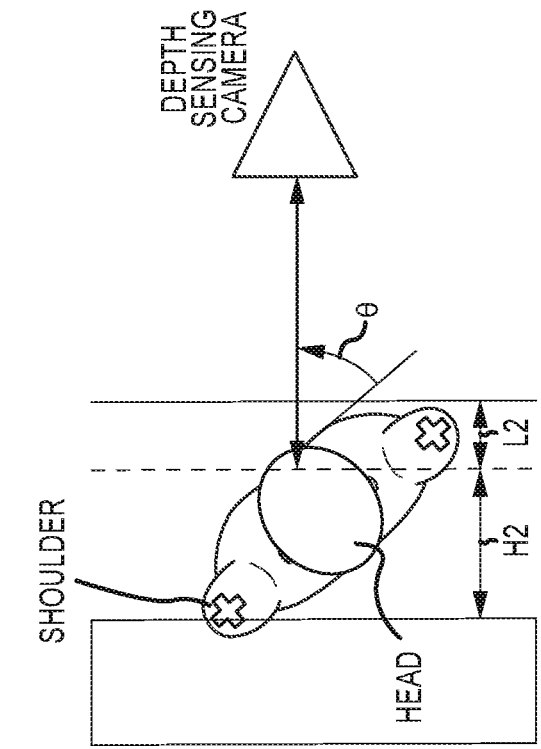
FIG. 37 is a diagram showing an alternate method for adjusting depth thresholds with respect to a patient based on locations of shoulders of the patient according to various embodiments described herein.
Figure 37:
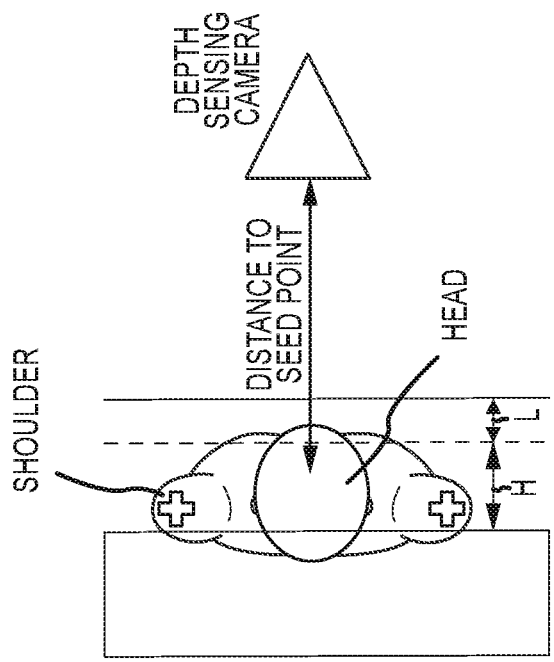

In some embodiments, the flood field depth range may be increased in magnitude by using the angle of incidence and/or the location of the peripheral (shoulder) point on the skeleton as illustrated in FIGS. 34-37. FIG. 34 is a diagram showing a representation of different depth thresholds associated with a patient orthogonal to a line of sight of a camera according to various embodiments described herein. FIG. 35 is a diagram showing a representation of unadjusted depth thresholds with respect to a patient that is not orthogonal to a line of sight of a camera according to various embodiments described herein. FIG. 36 is a diagram showing a representation of adjusted depth thresholds with respect to a patient that is not orthogonal to a line of sight of a camera according to various embodiments described herein. FIG. 37 is a diagram showing an alternate method for adjusting depth thresholds with respect to a patient based on locations of shoulders of the patient according to various embodiments described herein (e.g., that can be employed to ensure that the two shoulder joints of the patient always stay inside the flood fill range).

In particular, the thresholds H and L of FIGS. 34 and 35 are adjusted to H2 and L2 of FIG. 36 based on the angle $\theta$. In another embodiment shown in FIG. 37, H2 and L2 are adjusted from H and L based on known points of the body, such as the shoulder joints represented by the red crosses of FIG. 37. In a first example, H2 and L2 are adjusted according to a fixed tolerance amount, such as by adjusting H2 and L2 according to Equations 9 and 10, respectively, below:

$$H2 = \text{MAX}(H, \text{DISTANCE}(\text{SEED}, \text{FAR SHOULDER}) + \text{TOLERANCEAMOUNT}) \quad [9]$$

$$L2 = \text{MAX}(L, \text{DISTANCE}(\text{SEED}, \text{NEAR SHOULDER}) + \text{TOLERANCEAMOUNT}) \quad [10]$$

In a second example, H2 and L2 are adjusted according to a relative amount (e.g., 10%), such as by adjusting H2 and L2 according to Equations 11 and 12, respectively, below:

$$H2 = \text{MAX}(H, \text{DISTANCE}(\text{SEED}, \text{FAR SHOULDER}) *1.1) \quad [11]$$

$$L2 = \text{MAX}(L, \text{DISTANCE}(\text{SEED}, \text{NEAR SHOULDER}) *1.1) \quad [12]$$

This helps ensure that the motion of the chest is properly captured and that the ROI is properly determined such that tidal volume can be accurately calculated.

The discussion below with respect to FIGS. 38-43 further discuss how to address obstructions in the line of sight between a camera and a desired ROI on a patient. In some cases when the patient is completely obscured by an obstruction, a tidal volume output may be reported as invalid. However, in some cases with partial obstructions, for example from the hands of the patient moving in front of the camera, an ROI may be adjusted so that an accurate tidal volume can be determined. Various embodiments disclosed herein advantageously provide improvements for overcoming partial obstructions using a three-dimensional (3D) calibration procedure prior to real-time monitoring of tidal volume using a depth sensor camera system. In some embodiments, a hand may be resting flush with the chest. In such an instance, the hand may not be excluded from the ROI, as it may move along with the chest as the patient breathes. In some embodiments, the area where the hand is placed may be incorporated in a measurement of the tidal volume, but may be assigned a lower confidence value or excluded if the movement in the area of the hand differs significantly from movement of the chest showing around the hand. That is, the system may determine when the area of the hand can be used to accurately calculate tidal volume and when it should be excluded.

Figure 38:
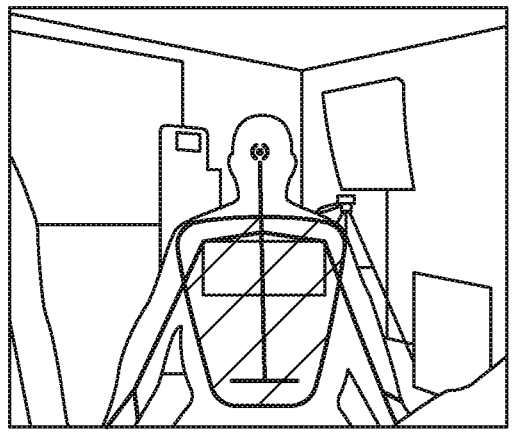
FIG. 38 is a diagram showing an ROI of a patient according to various embodiments described herein.
Figure 39:
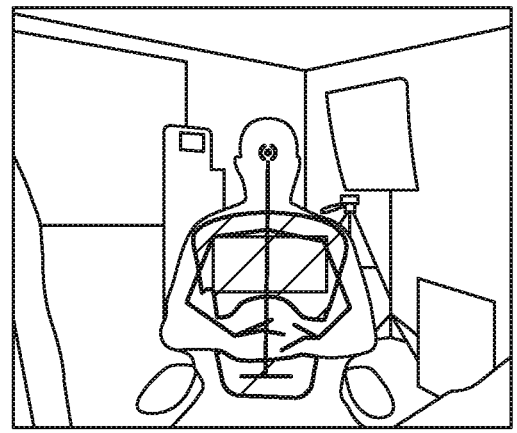
FIG. 39 is a diagram showing an ROI of a patient with a partial obstruction of the patient's hands according to various embodiments described herein.

FIG. 38 is a diagram showing an ROI of a patient according to various embodiments described herein. FIG. 39 is a diagram showing an ROI of a patient with a partial obstruction of the patient's hands according to various embodiments described herein. FIGS. 38 and 39 show the depth data obtained using a depth camera sensor as disclosed herein, showing the ROI without any obstruction in FIG. 38 and with partial obstruction of the ROI in FIG. 39.

Figure 40:
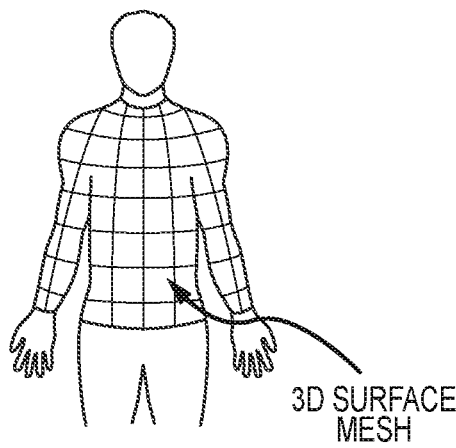
FIG. 40 is a diagram showing a patient with a three-dimensional mesh superimposed over the patient according to various embodiments described herein.
Figure 41:
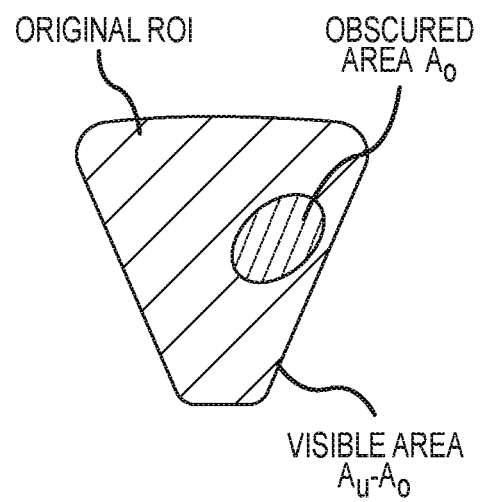
FIG. 41 is a diagram showing an ROI of a patient with an obscured area according to various embodiments described herein.

In an embodiment, a 3D body scan calibration process is performed at the start of measurement for the patient. FIG. 40 is a diagram showing a patient with a three-dimensional (3D) mesh superimposed over the patient according to various embodiments described herein. The 3D mesh is obtained from a calibration process that allows the mapping of a 3D chest surface profile of the patient. This calibrated 3D surface profile is used to estimate a portion of an ROI that has been obscured. The obscured region is identified, and the 3D profile is used to estimate the contribution to the tidal volume of the obscured region according to various embodiments discussed below.

In a first embodiment, the ratio of the original unobscured ROI (Au) to the visible area may be used to estimate the true tidal volume (TVe) from the measured tidal volume from the visible area (TVv)) as follows in Equation 13:

$$TVe = TVv(Au/(Au-Ao))  \qquad [13]$$

where Ao is the obscured area. This is shown schematically in FIG. 41, which is a diagram showing an ROI of a patient with an obscured area according to various embodiments described herein.

In other embodiments, the excursions around the obscured area may be used to estimate the excursions within the obscured area which are then multiplied by the obscured areas to provide the contribution to measured tidal volume from the unobscured area. This is shown schematically in FIG. 42, which is a diagram showing an ROI with an excluded obscured area according to various embodiments described herein. This may be done by measuring the average excursion ($\Delta_{ave}$) around the edge of the obscured region and using this to calculate the tidal volume contribution (TVc) as follows in Equation 14:

$$TV_c = A_o \times \Delta_{ave}  \qquad [14]$$

where Ao is the area of the obscured region. Alternatively, the relative excursions during the pre-obscured time within the obscured region are determined and used to estimate the excursions during the obscured time. This may be done by assigning excursion pro-rata based on proportional excursions across the mesh during the pre-obscured period.

In another embodiment, the data from the last previously unobstructed breath can be saved as a map of relative contribution to the measured tidal volume. An obstructed region's contribution can be calculated using this historical unobstructed map of ratios. Moreover, a confidence metric of the estimate can be deduced using this map, where, for example, C=1−Sum(Obstructed contributions). In this way, obstruction of low contribution areas would affect confidence less than obstruction of areas known to contribute more to the measured volume. In the absence of previous unobstructed breath, a generic map of contribution can be used which would be built based on accumulated patient data.

In another embodiment, feature points measurements (e.g., skeletal points such as shown in FIGS. 38 and 39) are recorded during the calibration process. These feature points represent fixed physical dimensions that will be used to calculate the position of the 3D body mesh due to the changes in orientation of the patient. Some examples of fixed point measurements are sternum to shoulder ends, height of chest, and width across stomach/belly/waist. If the total obscured region is within an acceptable tolerance, then the obscured region is reconstructed using the initial 3D mesh. The estimated 3D surface can be performed by comparing the unobscured regions with the 3D calibration scan, and re-mapping the obscured regions after obtaining the best morphological transform of the current position of the body. (This can be a translation, rotation, affine transformation due to different body position and respiration.)

Figure 43:
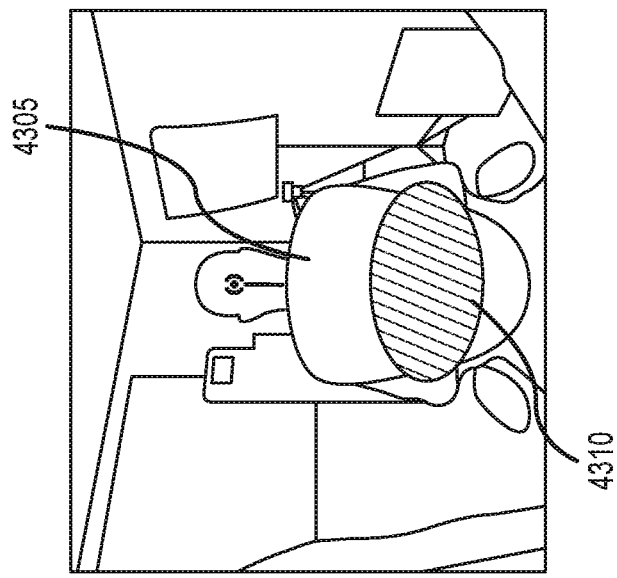
FIG. 43 is another diagram showing an ROI with an excluded obscured area according to various embodiments described herein.
Figure 42:
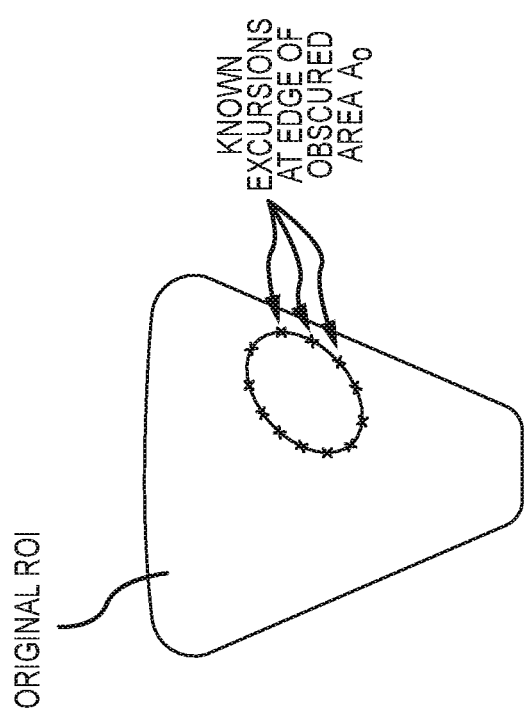
FIG. 42 is a diagram showing an ROI with an excluded obscured area according to various embodiments described herein.

In another embodiment, a reconstructed region is displayed in a different color scheme to the normal depth data. This provides a visual feedback to the operator which indicates the region that is based on estimated calculation. This is shown in FIG. 43, which is a diagram showing an ROI with an excluded obscured area according to various embodiments described herein. In particular, the larger, light gray region 4305 is a normal ROI covering the full chest region and the smaller oval with diagonal lines region 4310 indicates an obstruction present in that instance of measurement. A confidence level may also be calculated based on, for example, the ratio of visible area to total area. The confidence level may be displayed on the screen and/or may be used within the tidal volume algorithm. For the latter, it may, for example, be used to determine when the confidence is below a threshold and therefore the tidal volume should no longer be displayed.

Figure 45:
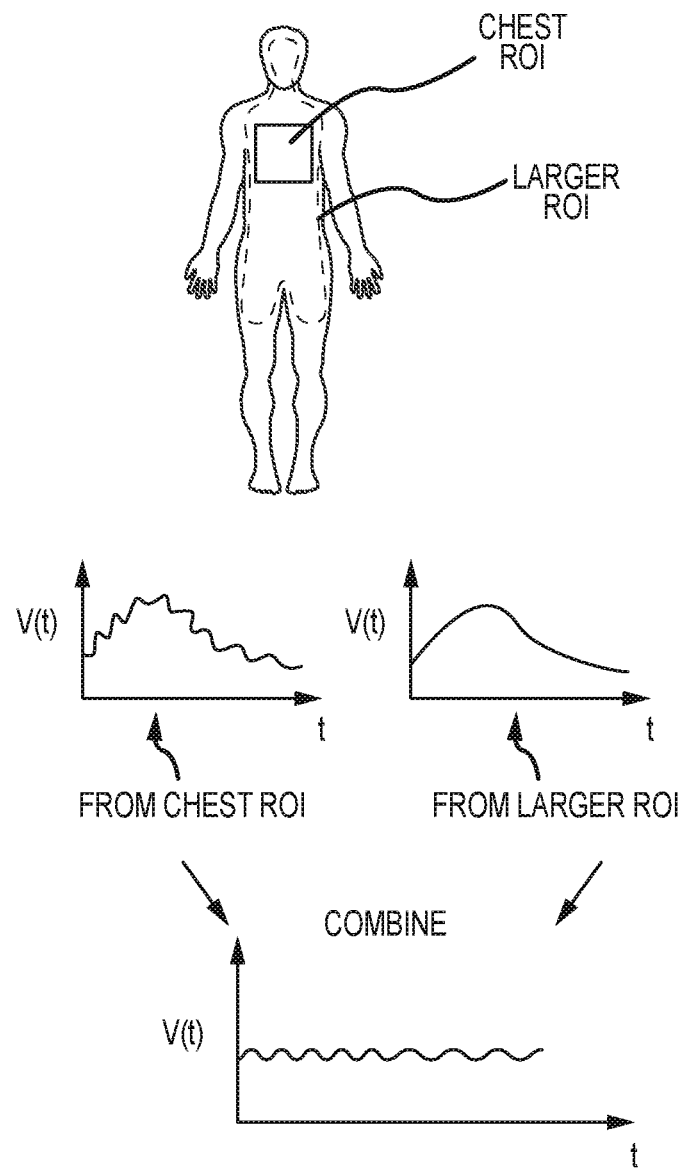
FIG. 45 is a diagram showing a patient with two differently sized ROIs for measuring tidal volume according to various embodiments described herein.
Figure 46:
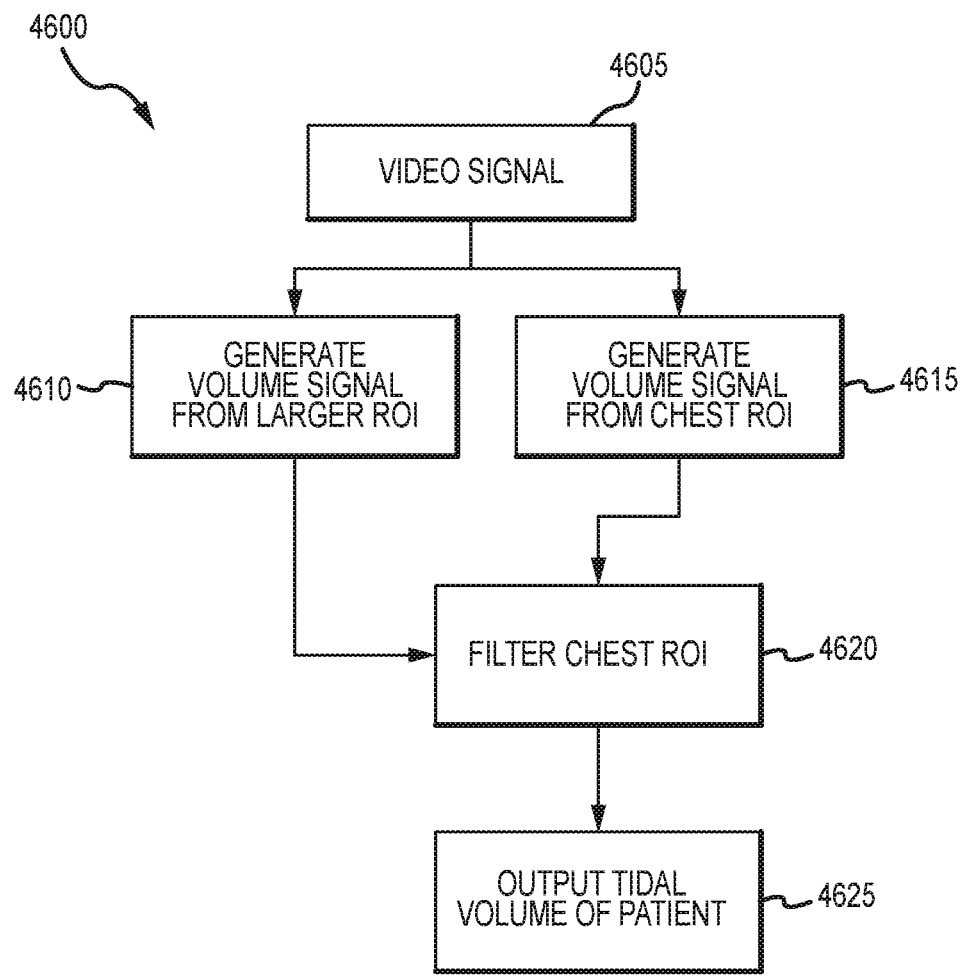
FIG. 46 is a flowchart showing a method for determining tidal volume using two differently sized ROIs according to various embodiments described herein.

Also disclosed herein are various systems, methods, and computer readable media for improving tidal volume measurements using non-contact video monitoring. For example, a volume signal may be corrupted with noise due to movement of the patient. In another example, certain movement of a patient related to respiration may not always be visible to a camera. Disclosed herein and discussed below with respect to FIGS. 44-46 are embodiments for mitigating noise and improving accuracy and robustness of tidal volume measurements.

Figure 44:
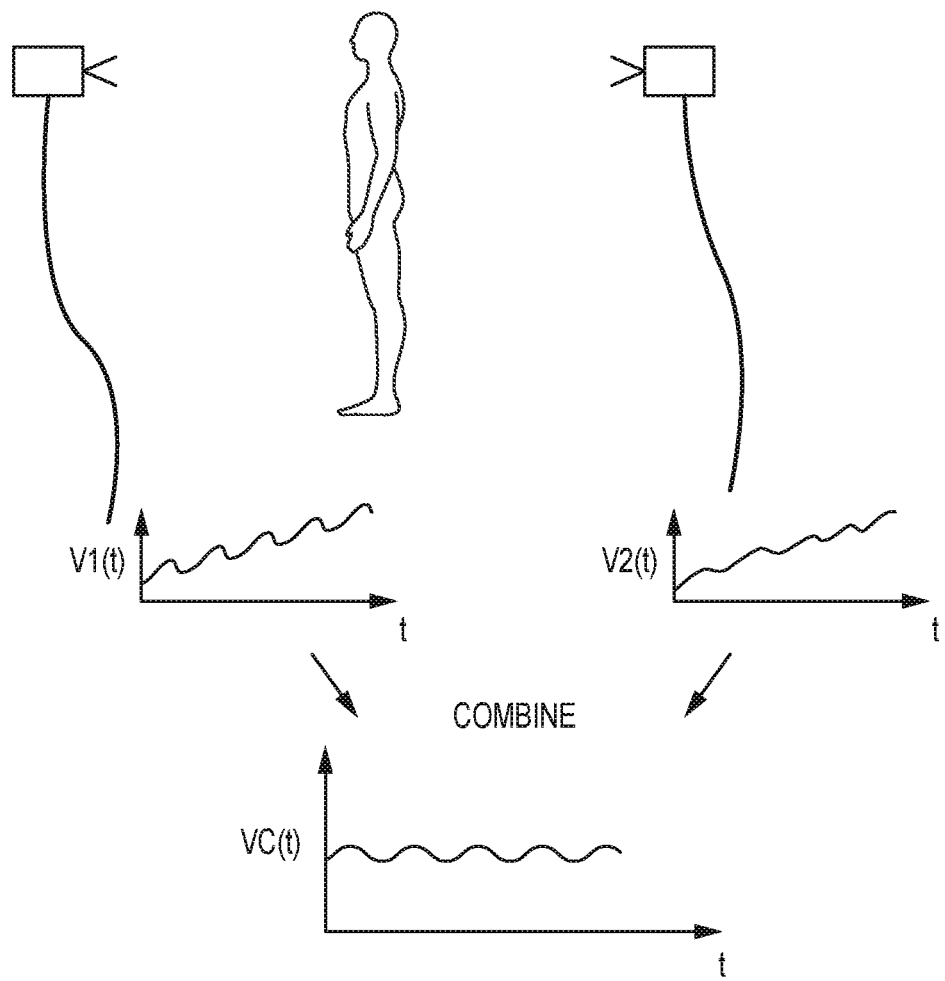
FIG. 44 is a diagram showing a two-camera system for determining ROIs of a patient and/or measuring tidal volume of the patient according to various embodiments described herein.

FIG. 44 is a diagram showing a two-camera system for determining ROIs of a patient and/or measuring tidal volume of the patient according to various embodiments described herein. In a multiple camera system, cameras may be oriented at the back and front of the patient as shown in FIG. 44. Such cameras can be used to produce two volume signals using various embodiments disclosed herein: V1(t) and V2(t). In a method V1(t) and V2(t) may be used to determine an actual tidal volume by subtracting one from the other. For example, the volume change signal may be determined as follows in Equation 15:

$$VC(t) = V1(t) - V2(t)  \qquad [15]$$

The initial values of VC(t) may be set to zero when the analysis is first activated. Alternatively, the minimum value of VC(t) may be set to zero. The method is outlined schematically in FIG. 44. In various embodiments, more than two cameras may be used to further improve the tidal volume measurement. In the example shown in FIG. 44, the volume signals V1(*t*) and V2(*t*) are associated with a first camera on the left and a second camera on the right, respectively. The signals V1(*t*) and V2(*t*) each trend up if they are configured such that the positive direction for each camera is the same. For example, if the positive direction for each camera is set as left to right in FIG. 44 then the signals V1(*t*) and V2(*t*) indicate that the patient is moving toward the camera on the right while breathing. If the positive direction for each camera is set as right to left in FIG. 44, then the signals V1(*t*) and V2(*t*) would indicate that the patient is moving toward the camera on the left while breathing. If, however, the cameras were set so that the positive direction was relative to each camera, the signals V1(*t*) and V2(*t*) would trend in opposite (rather than the same as in FIG. 44) directions when the patient moves toward one of the cameras and away from the other.

A multiple camera system may also be beneficial to track and measure shoulder movement. For example, in some patients, tidal volume may be measured at least in part by monitoring the movement/displacement of the shoulders. A depth sensing camera oriented generally orthogonal to a patient's chest may be able to detect some shoulder movement for the purpose of measuring tidal volume. However, one or more additional cameras (e.g., above a patient, to the right or left of a patient, behind a patient) may be able to capture additional movement in the shoulders that can be used to measure tidal volume.

Multiple camera systems can also be advantageously used to remove non-clinically relevant data. For example, patients may move throughout a room or in bed in a way that would impact the measurements made by a single camera and make it difficult to measure tidal volume. By utilizing multiple cameras, the movement of the patient can be tracked. For example, if a patient moves toward one camera and away from another, the depth vector measurements from the two cameras will capture that movement data in opposite directions and cancel one another out, leaving the movement associated with breathing to be measured as tidal volume. In such an embodiment, the system may determine an ROI on the chest of the patient using data from the first camera and a second ROI on the back of the patient using data from the second camera. Systems using more than two cameras in a similar way may also be used, and may add further robustness to the system.

In order to use two or more cameras to assess the patient's movement, position, and volume changes, in an embodiment, the cameras are able to determine where they are positioned and oriented with respect to each other. For example, in order to combine the depth measurements from each camera, the system needs to know if the two cameras are viewing in opposite directions, orthogonal directions, or any other angle or orientation. Because the tidal volume calculations can be made based on vectors in x, y, and z axes, the system can identify a calibration point(s) in the room to adequately define the axes, which may be particularly useful in embodiment where multiple cameras do not have line of sights that are orthogonal to one another. The cameras can determine their relative orientation by viewing a common object or calibration point in the room. That is, in one embodiment, an object or point in the room is visible within the field of view of both (or all) cameras. A calibration point may be a point on the patient such as a top of the head, or may be something in the room. The point identified in the room may be a specially configured device such as a sticker or sign with a bar code or other feature on it that can be recognizable from data captured by a camera. By identifying the same point or points in the room and using depth sensing data to determine where the camera is compared to the known object, point, or points, the system can accurately determine how measurements from each depth sensing camera can be mapped into vectors on the x, y, and z axes. In other words, the point(s) in the room can be used to identify where the cameras are actually located, and where the cameras are located with respect to one another.

In some embodiments, the cameras may send communications that can be captured by one another in order to calibrate them. For example, a camera may flash a light or send another signal to indicate its position. In another example, the depth sensing camera may capture data indicative of a camera so that the system can determine the location of a camera within another camera's field of view. This information can also be used to synchronize the data captured, i.e., make sure movement captured by the cameras are mapped as vectors onto the same axes so that tidal volume can be accurately determined. A three-dimensional object in the room may also be identified and used to calibrate/locate the cameras. In other words, information about the object in the room can be used to figure out where the cameras are in relation to the object and therefore in relation to one another. If a camera moves or is adjusted in a way that affects its field of view, zoom, etc., that movement/adjustment can be tracked and accounted for when calibrating/locating the cameras and subsequently in tidal volume calculations.

In some embodiments, multiple cameras may be able to see an entire room or more. The system may include logic to use or prioritize data from certain cameras that have a better view of a patient or ROI. In this way, more accurate measurements can be made. If multiple cameras are used to determine ROI and/or tidal volume, some cameras may be determined to have a better view of the patient or otherwise can make more accurate measurements. In such cases, the system may weight the data from those cameras more heavily (assign it a higher weight) or assign it higher confidence levels, so that the data that is more likely to be accurate is prioritized when calculating a tidal volume or other metric.

Similarly, various embodiments may also utilize full 3D reconstruction using multiple depth cameras. The real time reconstruction of a 3D volume based on multiple depth cameras can be used to track the overall volume of a patient in real time. In other words, rather than determining ROIs on the patient's body, the system may track the entire body of a patient. The tidal volume is a component of the patient's overall volume and may be extracted as a proportion of the total volume change. The motion (skeleton detection/tracking) data provided by the various embodiments disclosed herein can be used to mitigate against changes caused by patient motion.

In various embodiments, a multiple ROI method using a single camera may also be used. A larger ROI may be used as well as a smaller ROI (e.g., the chest only ROI). The mean movement of the larger ROI may be used to filter out the global body motions from the chest ROI hence leaving the respiratory signal intact. This may be done by using an adaptive filter to remove from the chest ROI signal the non-respiratory motions identified in the larger ROI signal. The larger ROI may or may not include the chest ROI. An example of this embodiment is shown schematically in FIG. 45 showing a patient with two differently sized ROIs for measuring tidal volume according to various embodiments described herein.

Other filtering/processing may be performed to exclude information that is non-clinically relevant. For example, when patients are talking or eating they may have unusual tidal volumes and respiration patterns that are harder to track and may not be clinically relevant. Accordingly, the systems, methods, and computer readable media disclosed herein may be configured to identify periods where a patient is talking or eating or doing another activity which is desirable to exclude. For example, data from a depth sensing camera may indicate that the patient is talking: movement of mouth/lips, irregular respiration rate, etc. Other sensors may be used in conjunction with the camera to determine that a patient is talking, such as an audio sensor. If an audio sensor picks up audio typical of the human voice and the respiration rate is abnormal, for example, the system may identify that the patient is talking and not use the data collected to attempt to monitor or calculate tidal volume. Other irregular situations may also be identified, such as while a patient is eating. Depth sensing camera data may be used to determine that the patient is eating, for example through movement of the jaw similar to chewing, neck movement indicating swallowing, hands moving periodically to the mouth to feed, appearance of a straw-like shape in front of the patient's face, etc. By identifying instances where irregular breathing is likely, the system can filter out data collected during those periods so as not to affect tidal volume measurements, averages, or other calculations. Additionally, the determinations of scenarios like eating and talking where breathing is expected to be irregular may also be beneficial for alarm conditions. For example, in a scenario when a patient is talking, any alarm related to a tidal volume measurement may be suppressed by the system.

FIG. 46 is a flowchart for a method 4600 for determining tidal volume using two differently sized ROIs according to various embodiments described herein. The method 4600 includes a video signal 4605, from which a larger ROI is determined at 4610 and a smaller chest ROI is determined at 4615. The method 4600 further includes filtering the chest ROI at 4620. At 4625, the tidal volume of the patient is output.

Various embodiments may include filtering out non-physiological signals as disclosed herein. For example, an expected spectral bandwidth of breathing may be known and used to filter out non-respiratory signals from a volume signal. For example, a raw volume signal may be band-pass filtered between 0.10 and 0.66 Hz (corresponding to 10 second and 1.5 second breaths or 6 and 40 breaths per minute). Where movement falls outside of the frequency range, it may be excluded because it is unlikely to be movement associated with respiratory movement.

In some embodiments, the systems, methods, and computer readable media disclosed herein may be used to measure volumetric $CO_2$. For example, when used in conjunction with a nasal cannula or other capnography device, volumetric $CO_2$ can be determined. In particular, a capnography device measures the percentage of carbon dioxide in the air being breathed out by a patient. With a tidal volume measurement as disclosed herein, the percentage of carbon dioxide in the air can be multiplied by the tidal volume to determine the volumetric $CO_2$ of the patient (i.e., how much total volume of carbon dioxide the patient is breathing out).

Various other data processing and filtering processes may be used on data gathered using depth sensing cameras or other devices for monitoring a patient. For example, trends may be monitored in the data, moving averages, weighted averages, and filtering to remove non-conforming data may all be utilized. Confidence levels may also be utilized to determine whether to include data. For example, a non-conforming behavior like talking may be identified to a predetermined threshold confidence level. If the non-conforming behavior is identified to that certain confidence level, then the data collected during that time can be excluded from trends, averages, and other data processing and/or gathering operations performed by the system. The system may also calculate confidence levels with respect to the tidal volume being measured. For example, if a robust ROI is determined, the system may have a higher confidence level with respect to the tidal volume calculated. If the patient is too obstructed, too far away, or other factors that are known to cause issues with tidal volume measurement is present, the system may associate a low confidence level with the tidal volume measurement. If a confidence level falls below a particular threshold level, the data collected during that time can be excluded from certain calculations with respect to the patient and their tidal volume. In some embodiments, confidence level thresholds may also be used to determine whether to propagate an alarm or not. For example, if a patient has left the room, the system will measure zero tidal volume. However, the system may recognize that it has not identified an ROI, giving a zero-confidence level in that measurement. Accordingly, alarm conditions with respect to the zero-tidal volume measurement will be suppressed. In more nuanced examples, the system may recognize when irregular situations are occurring, and use confidence levels to determine whether data collected is valid or invalid (i.e., should it be used in various calculations and/or recordkeeping of the system). By determining whether certain data is valid or invalid, the system can determine whether to use that data collected to calculate tidal volume of a patient.

Disclosed herein are also various types of alerts that may be used in accordance with tidal volume monitoring systems, methods, and computer readable media. For example, an alert may be triggered when a hypoventilation as described herein is detected. An alert may also be triggered if a tidal volume falls below a predetermined threshold. An alert may be triggered if a minute volume falls below a predetermined threshold. An alert may be triggered if no breathing activity is detected, or if no breathing activity is detected for at least a certain duration of time.

A system may also distinguish certain types of movement. For example, a patient's breathing patterns may change while sleeping. Accordingly, the system may determine if a patient is sleeping, how long they sleep, whether and how much they wake up in the night, etc. The determination of certain types of movement may also be patient specific. That is, certain patients may move in different ways for different types of movement. For example, a sleeping patient A may move differently than a sleeping patient B. The system may be able to identify differences in sleep patterns between patients. The system may also be able to identify sleep and awake states of a patient, even if those states vary in movement signatures by patient. For example, the system may identify that a patient is awake based on breathing patterns, tidal volume, respiration rate, minute volume, and/or other factors. By monitoring those factors, the system may be able to detect a change in those factors indicating that a patient is likely asleep. The system can then study the sleeping times for trends to determine a signature of that particular patient while they are sleeping. The system can then watch for data or signals similar to that signature in the future to determine that the patient is asleep.

The systems and methods described herein may be provided in the form of tangible and non-transitory machine-readable medium or media (such as a hard disk drive, hardware memory, etc.) having instructions recorded thereon for execution by a processor or computer. The set of instructions may include various commands that instruct the computer or processor to perform specific operations, such as the methods and processes of the various embodiments described herein. The set of instructions may be in the form of a software program or application. The computer storage media may include volatile and non-volatile media, and removable and non-removable media, for storage of information such as computer-readable instructions, data structures, program modules or other data. The computer storage media may include, but are not limited to, RAM, ROM, EPROM, EEPROM, flash memory or other solid-state memory technology, CD-ROM, DVD, or other optical storage, magnetic disk storage, or any other hardware medium which may be used to store desired information and that may be accessed by components of the system. Components of the system may communicate with each other via wired or wireless communication. The components may be separate from each other, or various combinations of components may be integrated together into a medical monitor or processor, or contained within a workstation with standard computer hardware (for example, processors, circuitry, logic circuits, memory, and the like). The system may include processing devices such as microprocessors, microcontrollers, integrated circuits, control units, storage media, and other hardware.

Although the present invention has been described and illustrated in respect to exemplary embodiments, it is to be understood that it is not to be so limited, since changes and modifications may be made therein which are within the full intended scope of this invention as hereinafter claimed.

What is claimed is:

1. A method of determining tidal volume of a patient, comprising:
   receiving, using a processor, at least one image comprising depth information for at least a portion of the patient;
   determining, using the processor, a reference point on the patient;
   determining, using the processor, a region of interest based at least in part on the reference point, wherein the region of interest corresponds to a trunk area of the patient;
   monitoring changes in the depth information in the region of interest over time;
   receiving, using the processor, demographic information about the patient; and
   determining, using the processor, a tidal volume of the patient based on the monitored changes in depth information and the received demographic information.

2. The method of claim 1, wherein the region of interest is further defined based on at least one body coordinate determined from the reference point.

3. The method of claim 2, wherein each of the at least one body coordinate corresponds to a location on a body of the patient, and wherein the location on the body of the at least one body coordinate is at least one of a shoulder, a hip, a neck, a chest, and a waist.

4. The method of claim 1, wherein the region of interest is further determined based on a distance of various portions of the patient from a camera that captures the at least one image.

5. The method of claim 1, wherein the region of interest is further determined by discarding various portions of a flood fill in response to determining that the patient is rotated such that the patient is not orthogonal to a line of sight of a camera that captures the at least one image.

6. The method of claim 1, wherein the region of interest is further determined by:
   determining that the trunk area of the patient is partially obscured; and
   excluding a partially obscured region from the region of interest.

7. The method of claim 1, wherein the at least a portion of the patient is at least a first portion of the patient, wherein the at least one image is captured using a first camera, and wherein at least a second image comprising at least a second portion of the patient is captured using a second camera.

8. The method of claim 7, further comprising determining, using the processor, a second region of interest of the patient based on at least the second image.

9. The method of claim 1, further comprising, determining, using the processor, a second region of interest of the patient from the at least one image.

10. The method of claim 9, wherein the region of interest is a different size than the second region of interest.

11. A video-based method of monitoring a patient comprising:
    receiving, using a processor, a video feed comprising a plurality of images captured at different times, wherein at least a portion of a patient is captured within the video feed;
    determining, using the processor, a region of interest of the patient on the video feed, wherein the region of interest corresponds to a trunk area of the patient;
    measuring, using the processor, changes to the region of interest over time;
    determining, using the processor, a tidal volume of the patient based on the changes to the region of interest;
    comparing, using the processor, the determined tidal volume to an output of an air flow measurement device to determine a patient-specific calibration factor, wherein the patient-specific calibration factor is applied to a relationship between the determined tidal volume and an adjusted tidal volume; and
    determining, using the processor, the adjusted tidal volume based on the determined tidal volume and the patient-specific calibration factor.

12. The method of claim 11, further comprising:
    receiving, using the processor, demographic information about the patient; and
    adjusting the determined tidal volume based on the demographic information.

13. The method of claim 12, wherein the demographic information comprises at least one of a sex, height, weight, body mass index (BMI), and age of the patient.

14. The method of claim 11, wherein a size of the region of interest is at least partially dependent on a distance of the patient from a camera that captures the video feed.

15. The method of claim 11, further comprising determining, using the processor, a change in the tidal volume of the patient over time.

16. The method of claim 15, further comprising determining, using the processor, a potential hypoventilation condition based on the change in the tidal volume of the patient.

17. The method of claim 11, wherein the region of interest is configured and/or the tidal volume of the patient is determined based on an orientation of the patient with respect to a camera that captures the video feed.

18. The method of claim 11, wherein the video feed is captured using a first camera, and a second video feed is captured using a second camera, wherein at least a second portion of the patient is captured within the second video feed.

19. The method of claim 18, further comprising determining, using the processor, a second region of interest of the patient based on the second video feed, wherein the tidal volume is further determined based on changes to the second region of interest over time.

* * * * *